(12) United States Patent
Ashwell et al.

(10) Patent No.: US 9,359,418 B2
(45) Date of Patent: Jun. 7, 2016

(54) INHIBITORS OF THE T CELL-SPECIFIC ALTERNATIVE P38 ACTIVATION PATHWAY AND METHODS OF USE

(71) Applicant: The United States of America, as represented by the Secretary, Department of Health and Human Services, Washington, DC (US)

(72) Inventors: Jonathan D. Ashwell, Chevy Chase, MD (US); Muhammad S. Alam, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/443,278

(22) PCT Filed: Nov. 19, 2013

(86) PCT No.: PCT/US2013/070813
§ 371 (c)(1),
(2) Date: May 15, 2015

(87) PCT Pub. No.: WO2014/081728
PCT Pub. Date: May 30, 2014

(65) Prior Publication Data
US 2016/0083442 A1 Mar. 24, 2016

Related U.S. Application Data

(60) Provisional application No. 61/728,368, filed on Nov. 20, 2012, provisional application No. 61/774,066, filed on Mar. 7, 2013.

(51) Int. Cl.
*C07K 14/00* (2006.01)
*C07K 14/475* (2006.01)
*A61K 38/00* (2006.01)

(52) U.S. Cl.
CPC ............... *C07K 14/475* (2013.01); *A61K 38/00* (2013.01); *C07K 2319/10* (2013.01)

(58) Field of Classification Search
None
See application file for complete search history.

(56) References Cited

U.S. PATENT DOCUMENTS 6,613,318 B1 9/2003 Wang et al.
7,326,418 B2 2/2008 Franzoso et al.

FOREIGN PATENT DOCUMENTS

WO WO 2005/077983 8/2005

OTHER PUBLICATIONS

Brand et al., "Collagen-Induced Arthritis," *Nature Protocols*, vol. 2:1269-1275, 2007.
Bulavin et al., "Loss of Oncogenic H-ras-Induced Cell Cycle Arrest and p38 Mitogen-Activated Protein Kinase Activation by Disruption of *Gadd45a*," *Mol. Cell. Biol.*, vol. 23:3859-3871, 2003.
GenBank Accession No. ACC54750, Apr. 20, 2008.
GenBank Accession No. AEI16541, Jun. 20, 2011.
Jirmanova et al., "Lack of the T Cell-Specific Alternative p38 Activation Pathway Reduces Autoimmunity and Inflammation," *Blood*, vol. 118:3280-3289, 2011.
Johnen et al., "The Role of Gadd45a in Suppression of Autoimmunity," *Mol. Cell. Pharmacol.*, vol. 1:290-298, 2009.
López-Santana et al., "Tyr$^{323}$-Dependent p38 Activation is Associated with Arthritis and Correlates with Disease Activity," *Arthritis Rheum.*, vol. 63:1833-1842, 2011.
Salvador et al., "Mice Lacking the p53-Effector Gene Gadd45a Develop a Lupus-Like Syndrome," *Immunity*, vol. 16:499-508, 2002.
Salvador et al., "Alternative p38 Activation Pathway Mediated by T Cell Receptor-Proximal Tyrosine Kinases," *Nat. Immunol.*, vol. 6:390-395, 2005.
Salvador et al., "The Autoimmune Suppressor Gadd45α Inhibits the T Cell Alternative p38 Activation Pathway," *Nat. Immunol.*, vol. 6:396-402, 2005.
Trabulo et al., "Cell-Penetrating Peptides—Mechanisms of Cellular Uptake and Generation of Delivery Systems," *Pharmaceuticals*, vol. 3:961-993, 2010.

*Primary Examiner* — Sheela J Huff
(74) *Attorney, Agent, or Firm* — Klarquist Sparkman, LLP

(57) ABSTRACT

In T lymphocytes, p38 mitogen activated protein kinase (MAPK) can be activated through an alternative pathway that involves phosphorylation at tyrosine 323. Disclosed herein is the identification of a minimal region of the growth arrest and DNA damage-inducible alpha (Gadd45α) protein that is required for binding to and inhibition of tyrosine 323-phosphorylated p38 in T cells. The disclosed Gadd45α polypeptides inhibit proliferation of T cells in response to T cell receptor stimulation, inhibit differentiation of T cells into Th1 or Th17 cells, inhibit the production of proinflammatory cytokines, and reduce tumor formation and growth of inflammatory cancers, such as pancreatic cancer.

21 Claims, 20 Drawing Sheets

FIG. 2
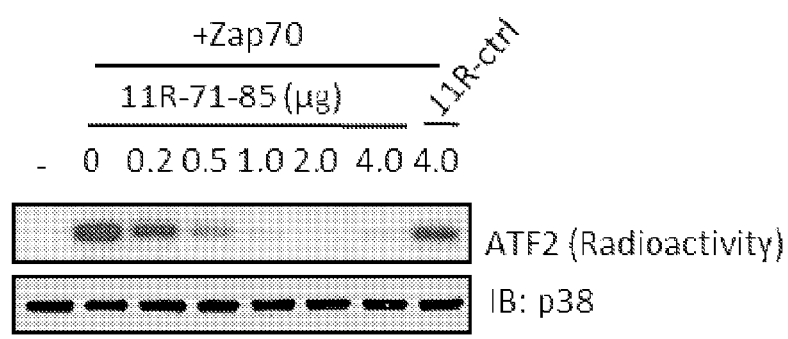
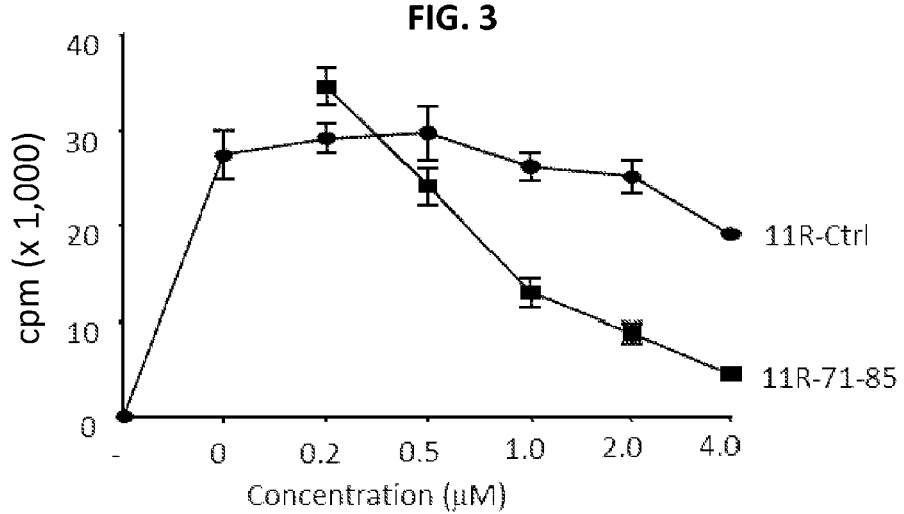

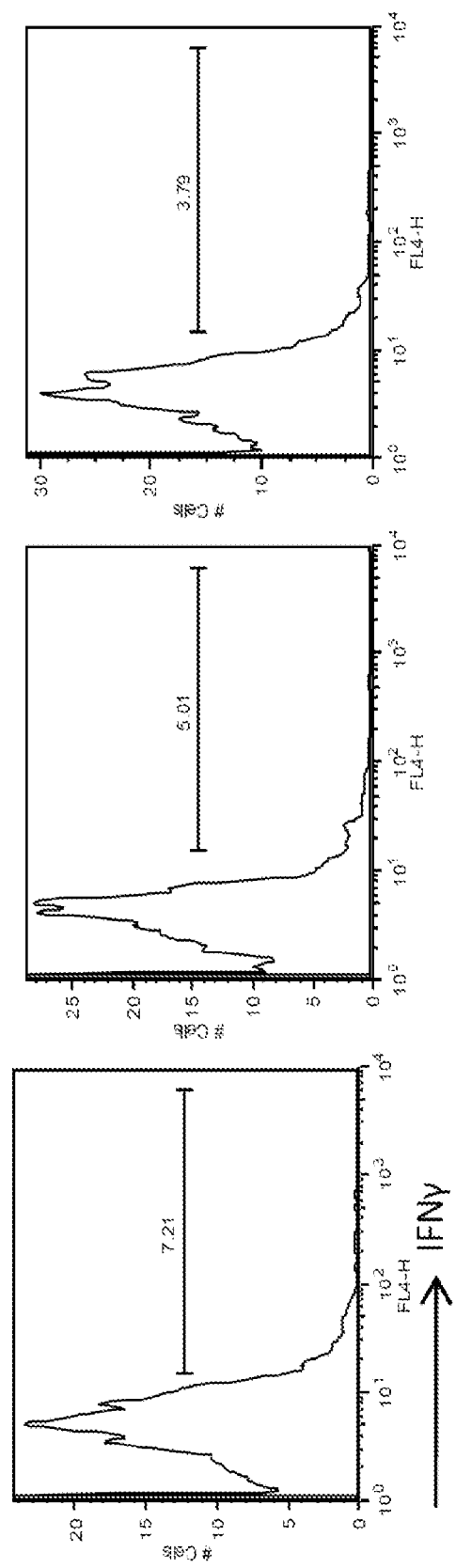

FIG. 8
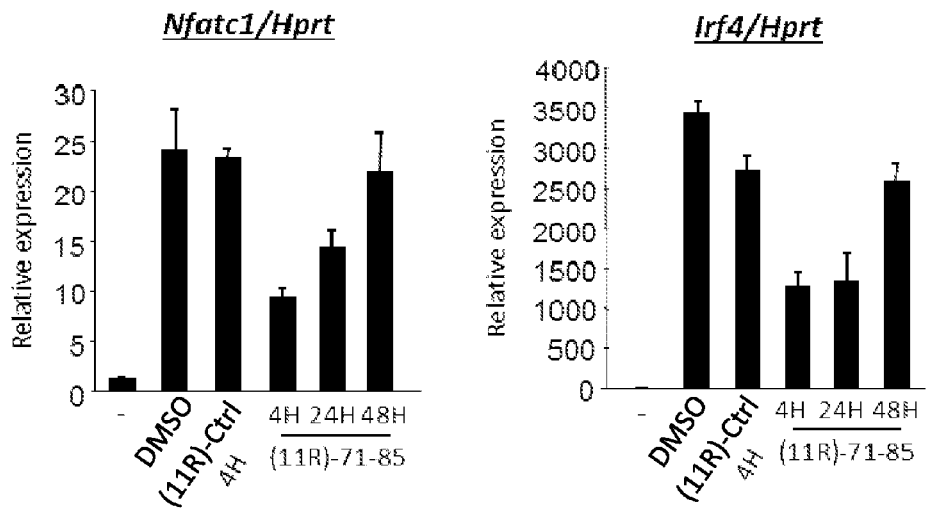
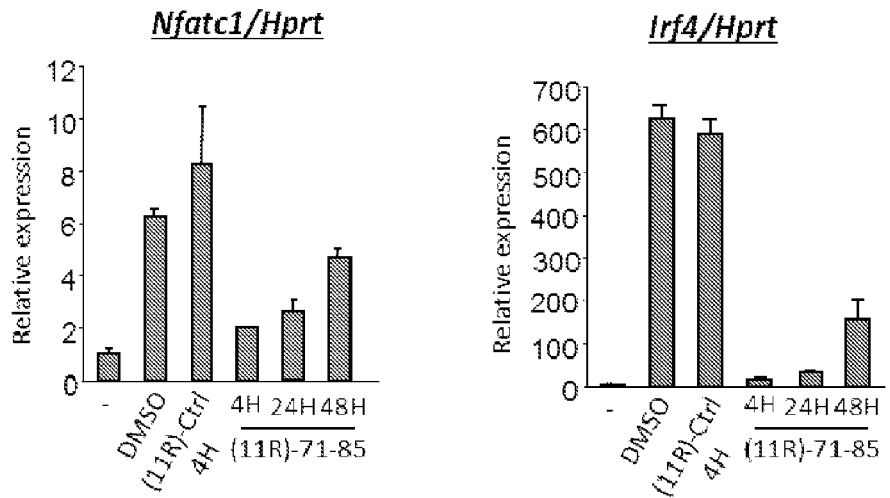

FIG. 11
CD31+ staining
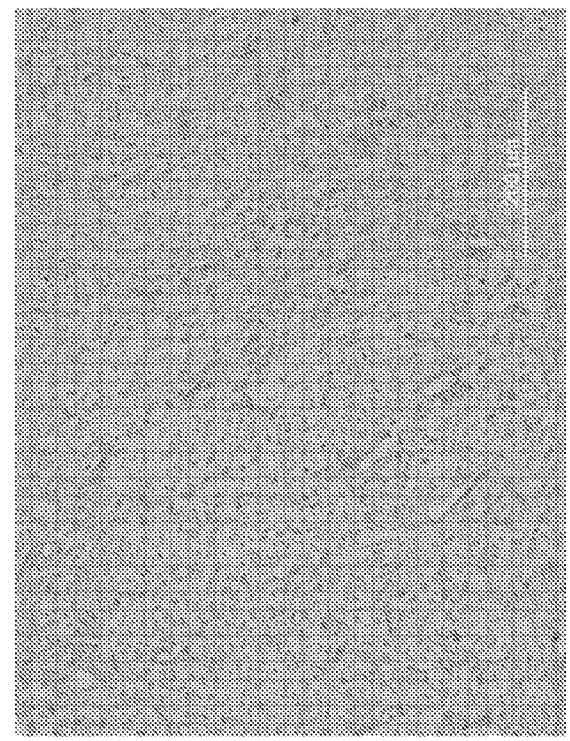
(11R) 71-85
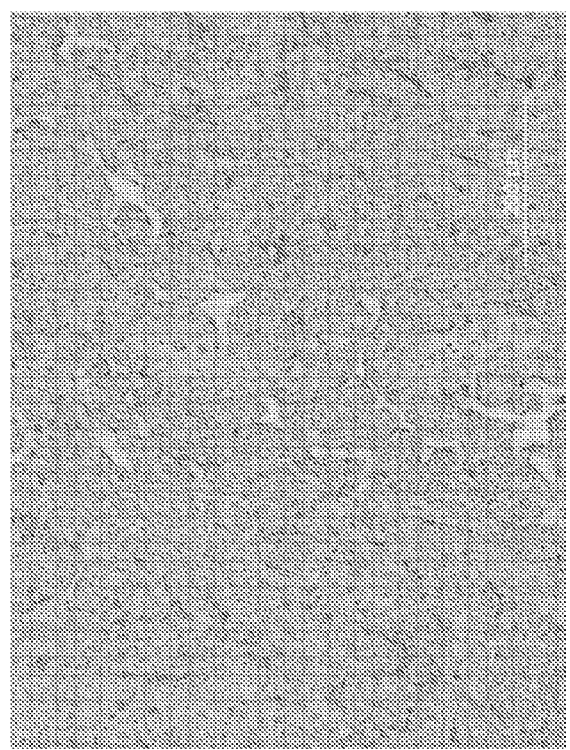
(11R) Scr

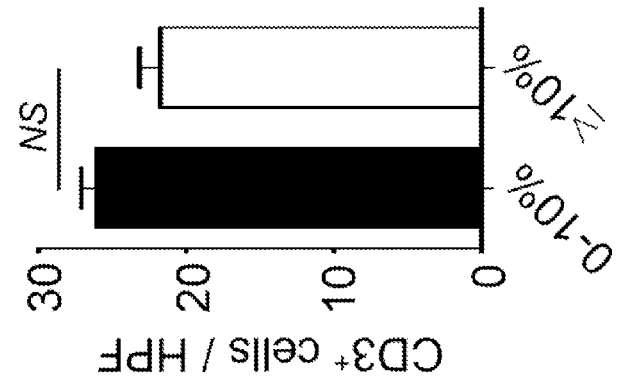
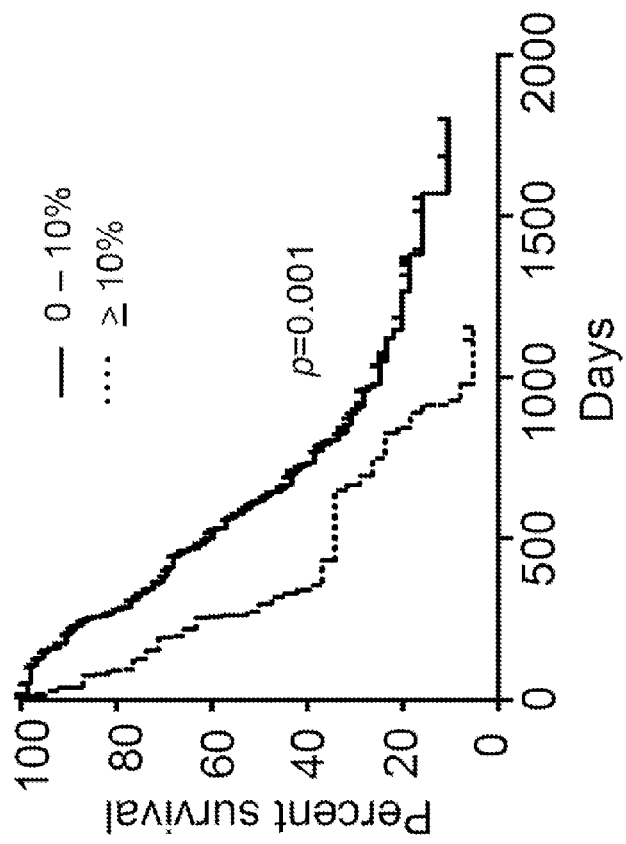

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (9)..(9)
<223> OTHER INFORMATION: Xaa = Gln or Arg

<400> SEQUENCE: 1

Leu Gln Ile His Phe Thr Leu Ile Xaa Ala Phe Cys Cys Glu Asn
1               5                   10                  15

<210> SEQ ID NO 2
<211> LENGTH: 15
<212> TYPE: PRT
<213> ORGANISM: Homo sapiens
```

```
<400> SEQUENCE: 2

Leu Gln Ile His Phe Thr Leu Ile Gln Ala Phe Cys Cys Glu Asn
1               5                   10                  15

<210> SEQ ID NO 3
<211> LENGTH: 15
<212> TYPE: PRT
<213> ORGANISM: Mus musculus

<400> SEQUENCE: 3

Leu Gln Ile His Phe Thr Leu Ile Arg Ala Phe Cys Cys Glu Asn
1               5                   10                  15

<210> SEQ ID NO 4
<211> LENGTH: 165
<212> TYPE: PRT
<213> ORGANISM: Homo sapiens

<400> SEQUENCE: 4

Met Thr Leu Glu Glu Phe Ser Ala Gly Glu Gln Lys Thr Glu Arg Met
1               5                   10                  15

Asp Lys Val Gly Asp Ala Leu Glu Glu Val Leu Ser Lys Ala Leu Ser
                20                  25                  30

Gln Arg Thr Ile Thr Val Gly Val Tyr Glu Ala Ala Lys Leu Leu Asn
            35                  40                  45

Val Asp Pro Asp Asn Val Val Leu Cys Leu Leu Ala Ala Asp Glu Asp
        50                  55                  60

Asp Asp Arg Asp Val Ala Leu Gln Ile His Phe Thr Leu Ile Gln Ala
65                  70                  75                  80

Phe Cys Cys Glu Asn Asp Ile Asn Ile Leu Arg Val Ser Asn Pro Gly
                85                  90                  95

Arg Leu Ala Glu Leu Leu Leu Leu Glu Thr Asp Ala Gly Pro Ala Ala
            100                 105                 110

Ser Glu Gly Ala Glu Gln Pro Pro Asp Leu His Cys Val Leu Val Thr
        115                 120                 125

Asn Pro His Ser Ser Gln Trp Lys Asp Pro Ala Leu Ser Gln Leu Ile
    130                 135                 140

Cys Phe Cys Arg Glu Ser Arg Tyr Met Asp Gln Trp Val Pro Val Ile
145                 150                 155                 160

Asn Leu Pro Glu Arg
                165
```

INHIBITORS OF THE T CELL-SPECIFIC ALTERNATIVE P38 ACTIVATION PATHWAY AND METHODS OF USE

CROSS REFERENCE TO RELATED APPLICATIONS

This is the U.S. National Stage of International Application No. PCT/US2013/070813, filed Nov. 19, 2013, published in English under PCT Article 21(2), which claims the benefit of U.S. Provisional Application No. 61/774,066, filed Mar. 7, 2013, and U.S. Provisional Application No. 61/728,368, filed Nov. 20, 2012, which are herein incorporated by reference in their entirety.

FIELD

This disclosure concerns inhibitors of the T-cell specific alternative p38 activation pathway and their use for the treatment of p38-associated diseases, such as autoimmune and inflammatory disorders, including inflammatory cancers. In particular, this disclosure concerns Gadd45α polypeptides capable of inhibiting p38 activation in T cells.

BACKGROUND

The p38 mitogen-activated protein kinase (MAPK) is a signaling intermediate downstream of proinflammatory cytokine receptors released following environmental stress. This kinase is known to play an important role in inflammatory and autoimmune diseases, including rheumatoid arthritis and multiple sclerosis. The p38 MAPK family includes four separately encoded members—p38α, p38β, p38γ and p38δ; p38α, p38β and p38δ are expressed in T cells, while p38γ is primarily expressed in skeletal muscle (Jirmanova et al., $Blood$ 118(12):3280-3289, 2011). The p38 kinase is ubiquitously expressed and is activated in all cells by a series of sequential phosphorylation steps that result in dual phosphorylation at threonine 180 and tyrosine 182. However, in T cells, direct stimulation of the T cells through their antigen receptor results in activation of an alternative p38 pathway, leading to phosphorylation of p38α and p38β on tyrosine 323 (Salvador et al., $Nat\ Immunol$ 6(4):396-402, 2005).

Genetically modified mice that express p38α and p38β containing a tyrosine to phenylalanine substitution at residue 323 (Y323F) have been developed and characterized to better understand the role of the T cell-specific alternative p38 activation pathway in vivo. Due to the phenylalanine substitution, the modified forms of p38α and p38β cannot be phosphorylated at residue 323, which prevents activation of the alternative p38 pathway. The genetically modified mice exhibit a significant reduction in T cell proliferation, proinflammatory cytokine production, as well as reduced susceptibility to animal models of autoimmune diseases such as multiple sclerosis and rheumatoid arthritis. Studies of these mice established that the alternative p38 activation pathway in T cells plays an important role in T cell activation and the development of autoimmune and inflammatory diseases (Jirmanova et al., $Blood$ 118(12):3280-3289, 2011).

Gadd45 (growth arrest and DNA damage-inducible genes) is a family of proteins that play a role in cell growth regulation, differentiation and apoptosis. In mammalian cells, three different Gadd45 family members have been identified—Gadd45α, Gadd45β and Gadd45γ. Using Gadd45α-deficient mice, prior studies have shown that Gadd45α inhibits the alternative p38 activation pathway, and the absence of Gadd45α results in T cell hyperproliferation and autoimmunity (Salvador et al., $Nat\ Immunol$ 6(4):396-402, 2005).

SUMMARY

Provided herein are growth arrest and DNA-damage-inducible alpha (Gadd45α) polypeptides capable of inhibiting the T-cell specific alternative p38 activation pathway. In some embodiments, the Gadd45α polypeptide is no more than 25 or no more than 20 amino acids in length and comprises residues 71-85 of human or mouse Gadd45α. In some cases, the Gadd45α polypeptides are synthetic or recombinant polypeptides (i.e. non-naturally occurring polypeptides). Also provided are fusion proteins comprising a Gadd45α polypeptide and a heterologous peptide, such as a cell-penetrating peptide. Further provided are compositions comprising the Gadd45α polypeptides and fusion proteins disclosed herein.

A method is also provided for inhibiting proliferation of T cells in response to T cell receptor stimulation by contacting the T cells with a Gadd45α polypeptide, fusion protein or composition disclosed herein. Further provided is a method of inhibiting differentiation of T cells into Th1 or Th17 cells by contacting the T cells with a Gadd45α polypeptide, fusion protein or composition disclosed herein. In some embodiments, the method is an ex vivo method wherein the T cells have been isolated from a subject. In other embodiments, the method is an in vivo method that includes administering the polypeptide, fusion protein or composition to a subject.

Methods of treating a subject having a T cell- and/or p38-mediated autoimmune or inflammatory disorder are also provided by the present disclosure. In some embodiments, the method includes selecting a subject with a T cell- and/or p38-mediated autoimmune or inflammatory disorder and administering to the subject a therapeutically effective amount of a Gadd45α polypeptide, fusion protein or composition disclosed herein.

Further provided herein is a method of inhibiting tumor vascularization in a subject. In some embodiments, the method includes selecting a subject with a tumor, for example a pancreatic tumor, and administering to the subject a therapeutically effective amount of a Gadd45α polypeptide, fusion protein or composition disclosed herein.

Also provided herein is a method of determining the prognosis of a subject diagnosed with pancreatic ductal adenocarcinoma (PDAC) by calculating the percentage of tumor-infiltrating T cells positive for p38 phosphorylated at tyrosine 323 (p38 pY323) in a tumor sample obtained from the subject; and determining that the subject has a poor prognosis if at least 10% of the T cells are positive for p38 pY323. In some embodiments, the poor prognosis is a decrease in time of survival.

The foregoing and other objects, features, and advantages of the disclosure will become more apparent from the following detailed description, which proceeds with reference to the accompanying figures.

BRIEF DESCRIPTION OF THE DRAWINGS

FIG. 2 shows inhibition of the p38 alternative pathway activation by (11R)-71-85. Purified p38 proteins were activated by incubating with active Zap70 in kinase buffer for 1 hour. (11R)-71-85 or (11R)-Ctrl was then added and incubated for 30 minutes at 30° C. One µg ATF2 and 10 µCi [$^{32}$P]ATP were then added and incubated for 45 minutes at 30° C. Phosphorylated products were resolved by SDS-PAGE, transferred to nitrocellulose membranes, and visualized by phosphorimager.

FIG. 3 is a graph showing T cell proliferation in response to (11R)-71-85. T cells were purified from spleen and treated with different concentrations of (11R)-71-85 or control peptide (11R)-Ctrl. Cells were then washed and stimulated with anti-CD3 and anti-CD28 for 2 days and finally pulsed with 1 µCi [$^3$H]-thymidine 14 hours before harvesting. [$^3$H]-thymidine uptake was determined with a Wallac 1450 MicroBeta Liquid Scintillation Counter.

Figure 4A:
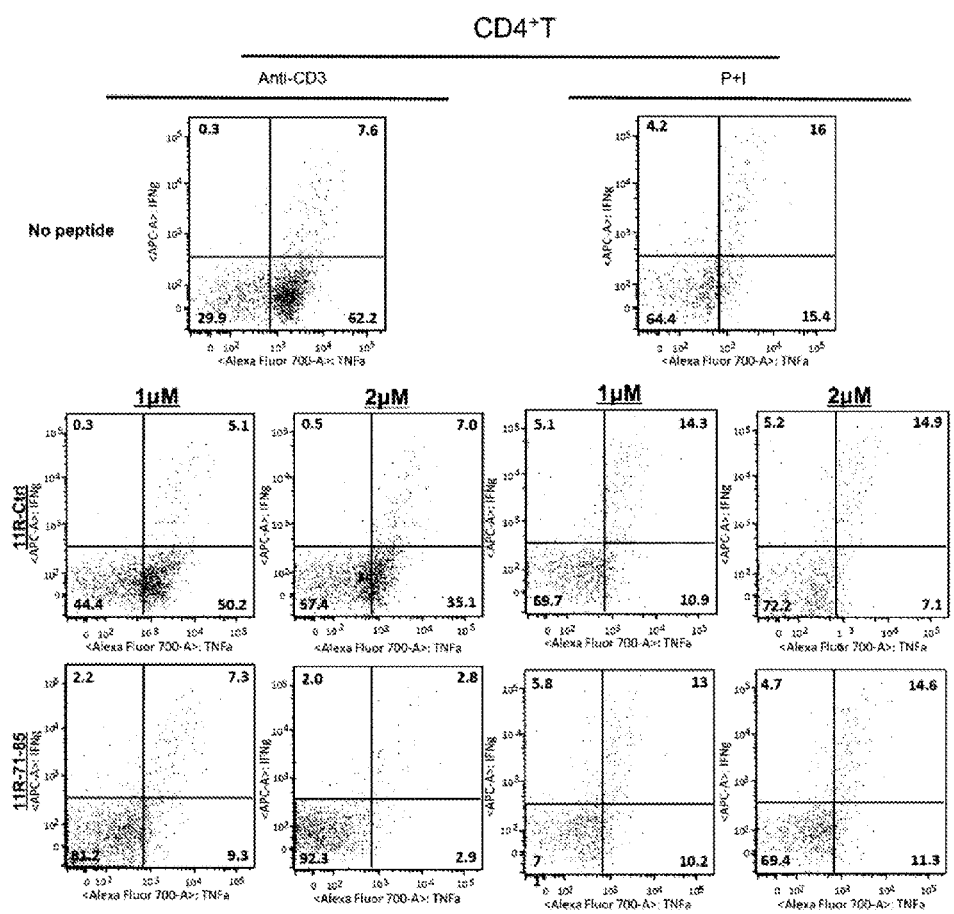
Figure 4B:
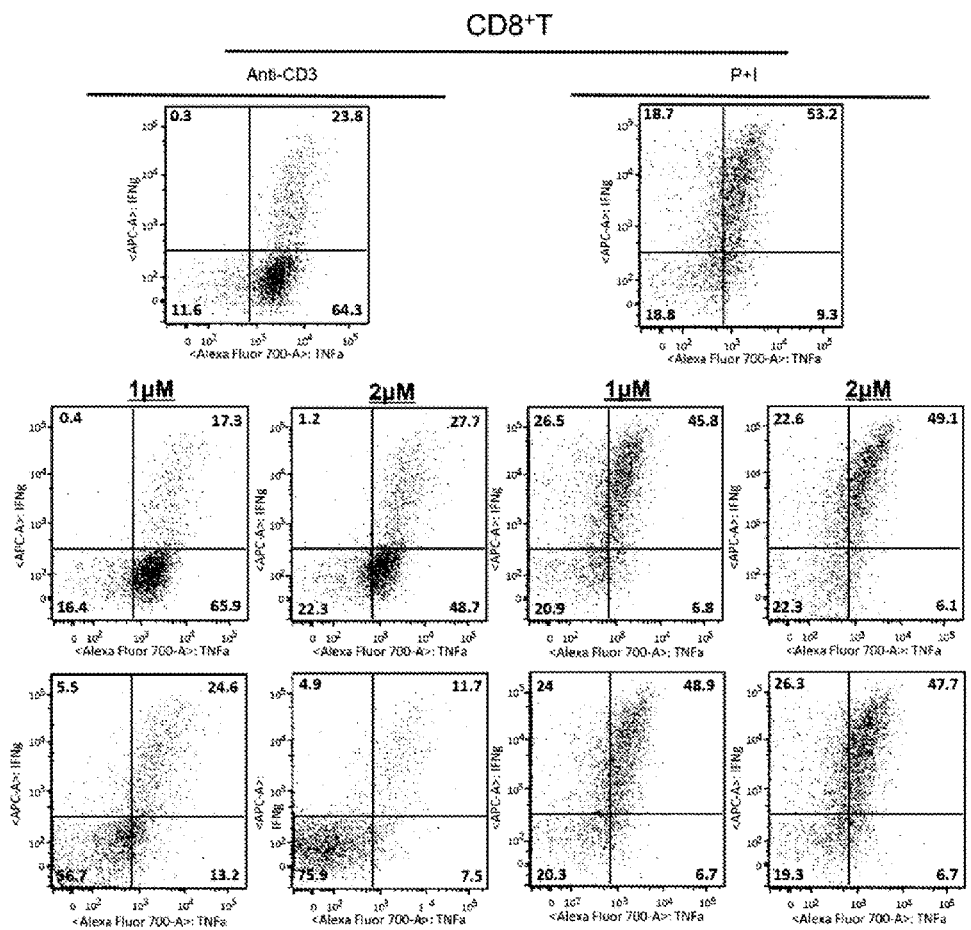
Figure 5A:
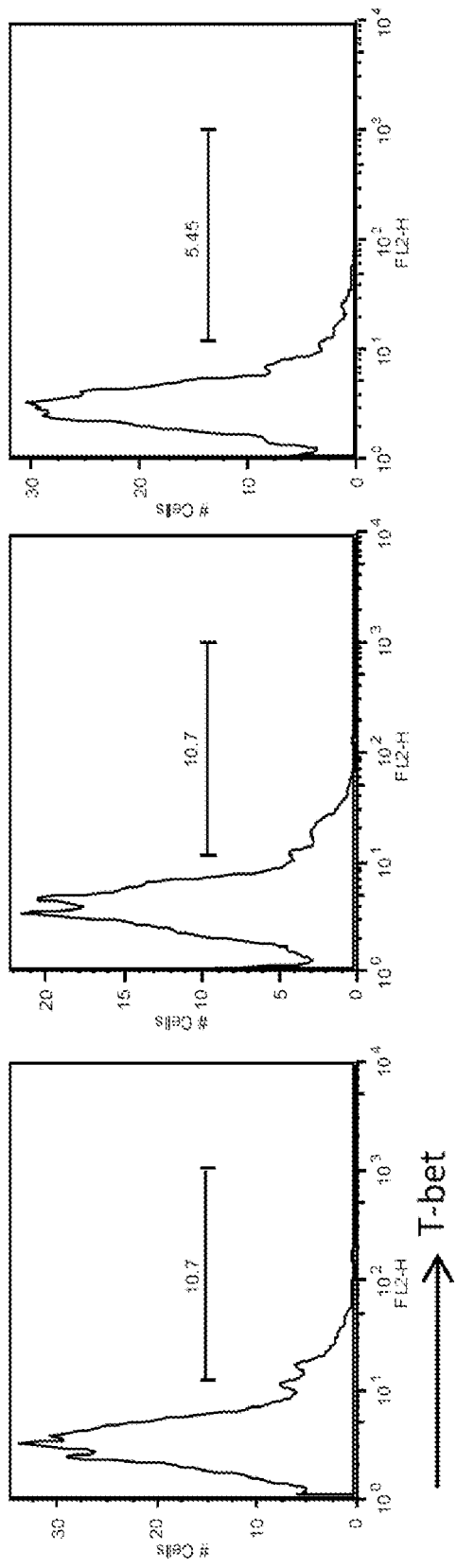
Figure 5B:
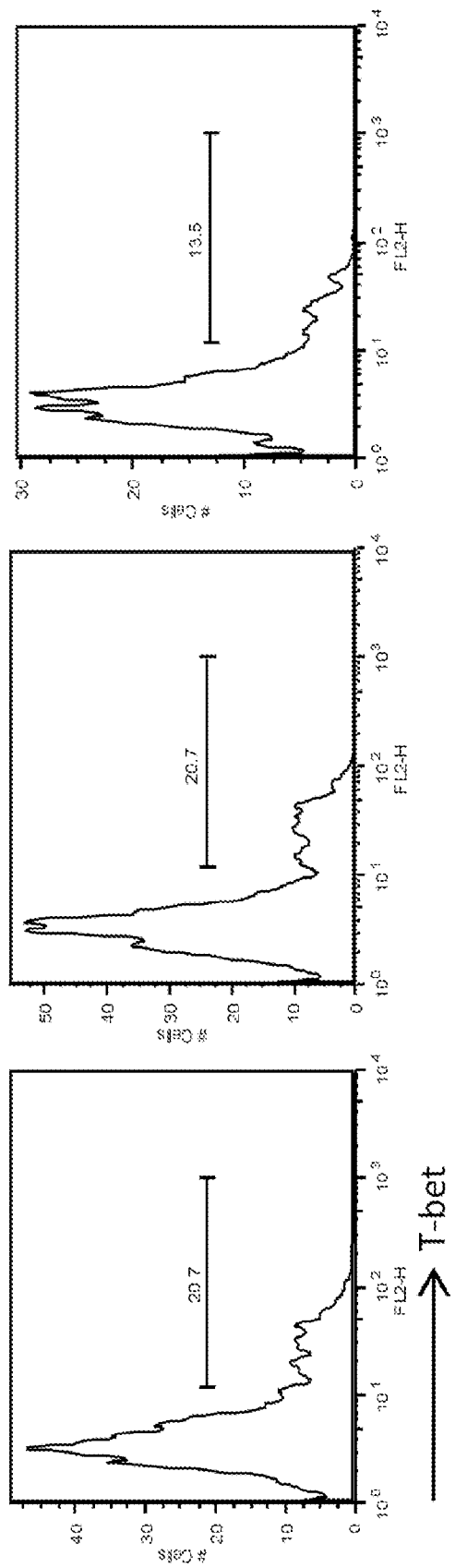
Figure 5D:
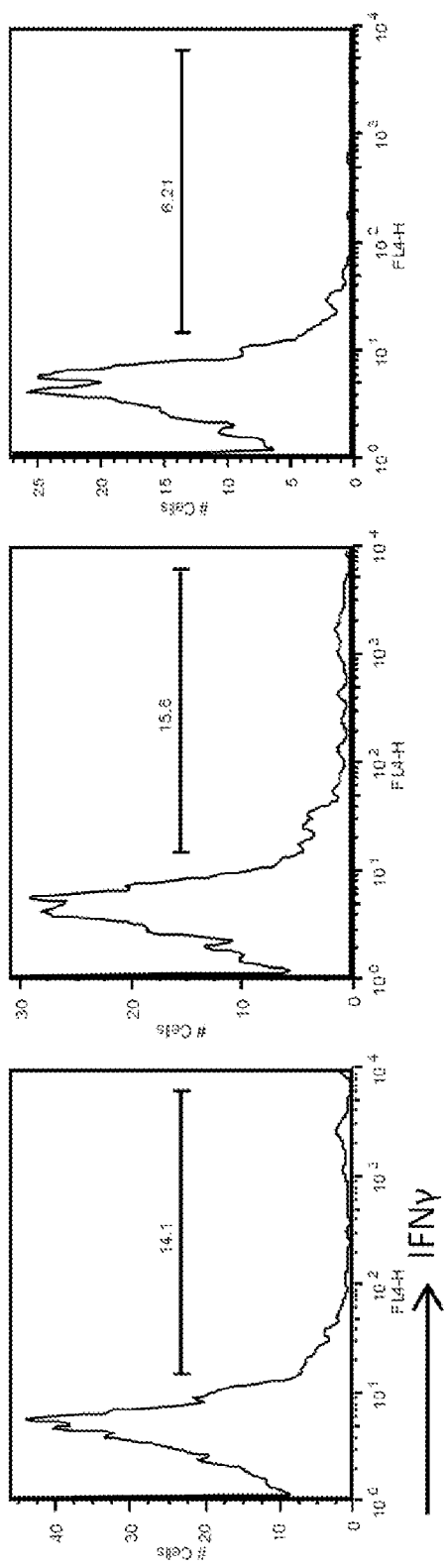

FIGS. 4A-4B are a series flow cytometry plots showing inflammatory cytokine secretion by CD4$^+$ (FIG. 4A) and CD8$^+$ (FIG. 4B) T cells. T cells were purified from spleen and stimulated with anti-CD3 plus anti-CD28 for 3 days. Cells were then left unstimulated overnight and treated with the indicated concentrations of (11R)-71-85, control peptide (11R)-Ctrl, or DMSO (no peptide). After treatment, cells were restimulated with either anti-CD3 plus anti-CD28, or PMA plus ionomycin supplemented with monensin. Cytokine expression was measured by flow-cytometry.

FIGS. 5A-5D are a series of flow cytometry plots showing (11R)-71-85 inhibits Th1 differentiation. Naïve CD4$^+$ T cells were treated with either 2 µM of (11R)-71-85 or (11R)-Ctrl for two hours and after washing, cells were stimulated with anti-CD3 plus anti-CD28 in Th0 (neutral, FIG. 5A and FIG. 5C) or Th1 polarizing conditions (FIG. 5B and FIG. 5D) for 3 days. Cells were treated again with the same concentration of either medium (first column), (11R)-Ctrl (second column), or (11R)-71-85 (third column) for 2 hours and restimulated with PMA plus ionomycin in the presence of Golgi inhibitor for 4 hours. Expression of T bet and interferon (IFN)-γ (indicators of Th1 cells typical of a pro-inflammatory response) was analyzed by flow cytometry. Whereas cells treated (11R)-Ctrl responded similar to cells treated with medium, the induction of T-bet and IFNγ was blunted by treatment with (11R)-71-85.

Figure 6A:
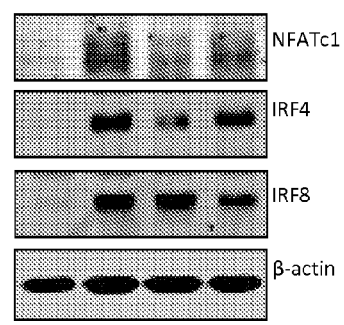
Figure 6B:
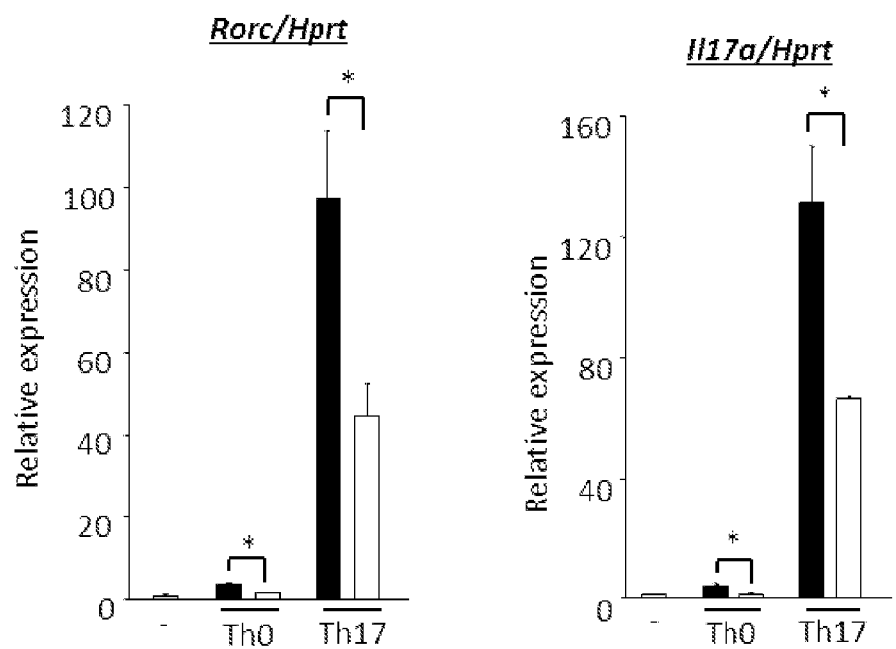

FIGS. 6A and 6B show inhibition of Th17 differentiation by full-length Gadd45α. (FIG. 6A) Purified CD4$^+$ T cells from WT mice were treated with 4 µM of either TAT-Ctrl, TAT-G45FL or TAT-G45Δ10 and stimulated with plate coated anti-CD3 plus anti-CD28 for 48 hours and blotted for the indicated transcription factors. (FIG. 6B) Naïve CD4$^+$ T (CD4$^+$ CD62L$^{hi}$) cells were purified from WT mice and treated with either TAT-Ctrl or TAT-G45FL as in (A) and stimulated in neutral (Th0) or Th17 skewing conditions (10 ng/ml IL-6+5 ng/ml TGF-β) for 48 hours. The mRNA expression levels of Rorc and Il17a were evaluated. P value of ≤0.05 was considered as a statistically significant difference and designated with an asterisk (*).

Figure 7:
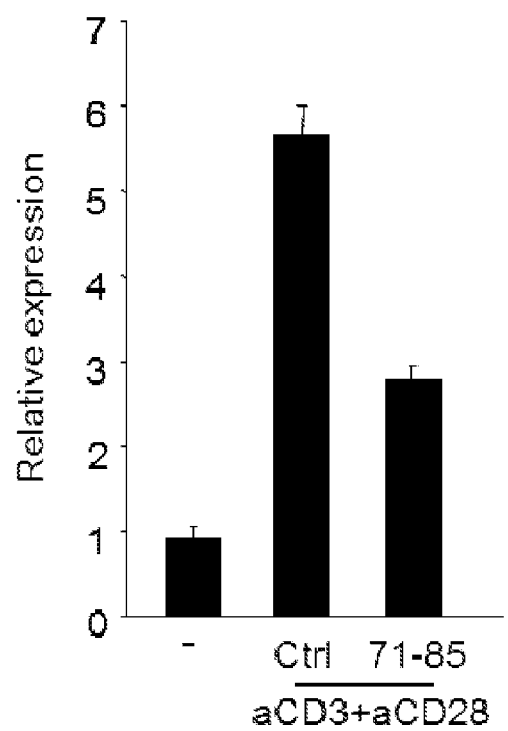

FIG. 7 is a graph showing expression of interferon regulatory factor 4 (Irf4) mRNA following in vivo treatment with (11R)-71-85. (11R)-71-85 (40 µg) or vehicle control was injected intraperitoneally into wild type mice. Four hours after injection, splenocytes were collected and stimulated with soluble anti-CD3 plus anti-CD28 for 24 hours. Irf4 mRNA expression was assessed by quantitative real time PCR.

FIG. 8 is a series of graphs showing reduction in expression of Nfatc1 and Irf4 in CD4$^+$ T cells following injection of (11R)-71-85. WT C57BL/6 mice were injected i.v. with 50 µg of DMSO, (11R)-Scrambled, or (11R)-71-85 and either total T cells or CD4±T cells were purified from spleen at different times. Purified cells were stimulated in vitro with anti-CD3/CD28 for 24 hours and the mRNA levels of the indicated transcription factors were determined by quantitative real-time PCR.

Figure 9C:
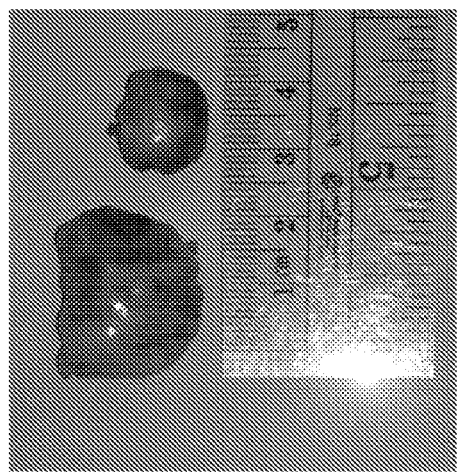
Figure 9B:
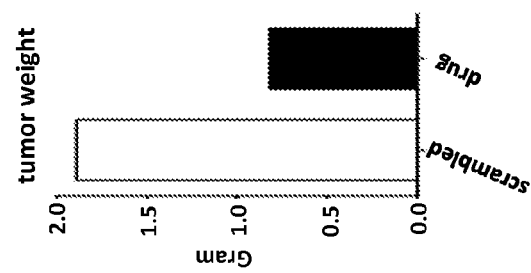
Figure 9A:
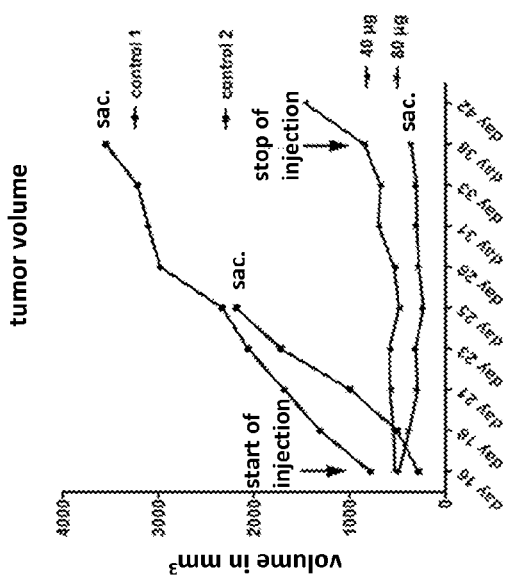

FIGS. 9A-9C show injection of (11R)-71-85 stops the growth of established PANC02 tumors. WT C57BL/6 mice were injected with 7.5×10$^5$ PANC02 cells. After 16 days, mice received intra-tumor injections of (11R)-71-85 at the indicated amount or DMSO every other day. (FIG. 9A) Tumor volume from the start of injection (day 16) to day 42 in control mice and mice injected with 40 µg or 80 µg of (11R)-71-85. Sacrifice (sac.) of mice before day 42 is indicated. (FIG. 9B) weight and (FIG. 9C) appearance of the control (left) and treated (right) tumors on day 38.

Figure 10A:
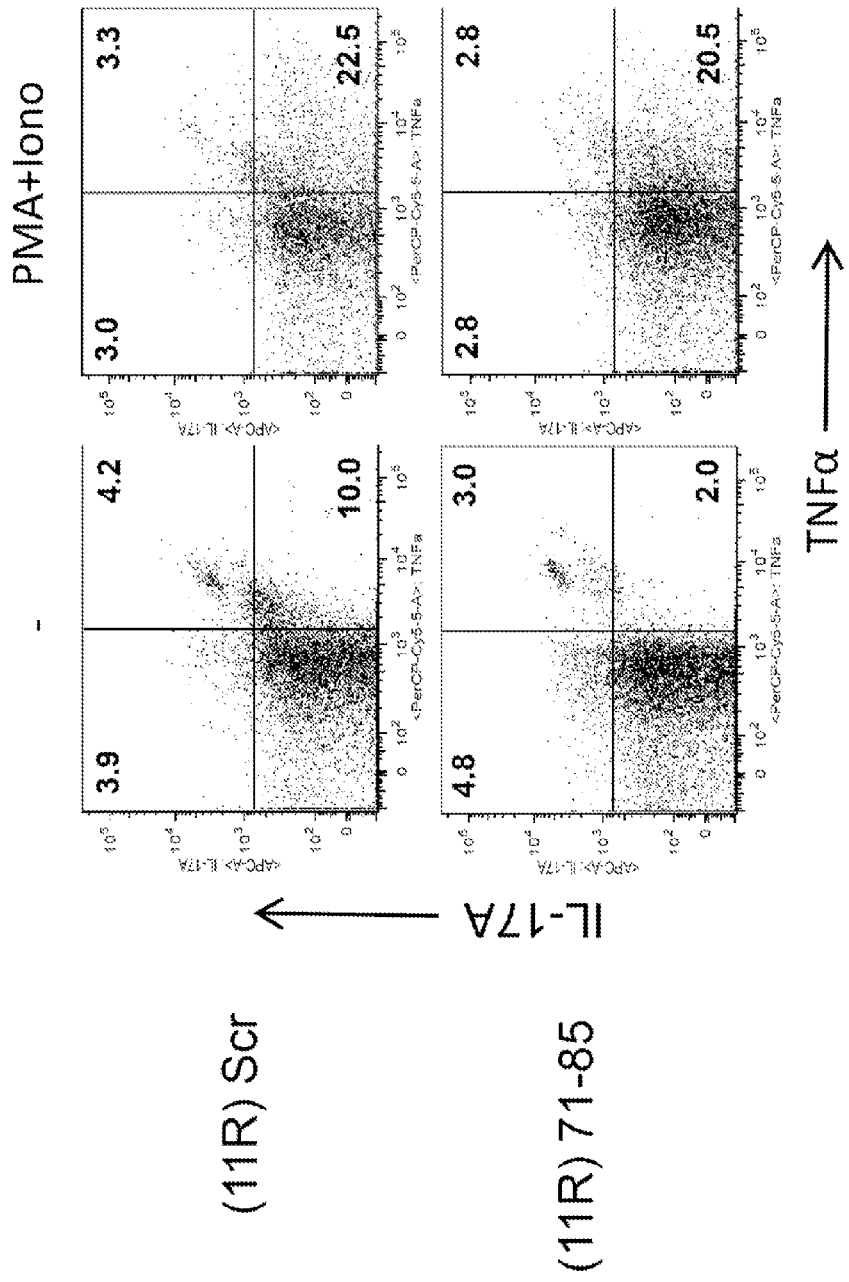
Figure 10B:
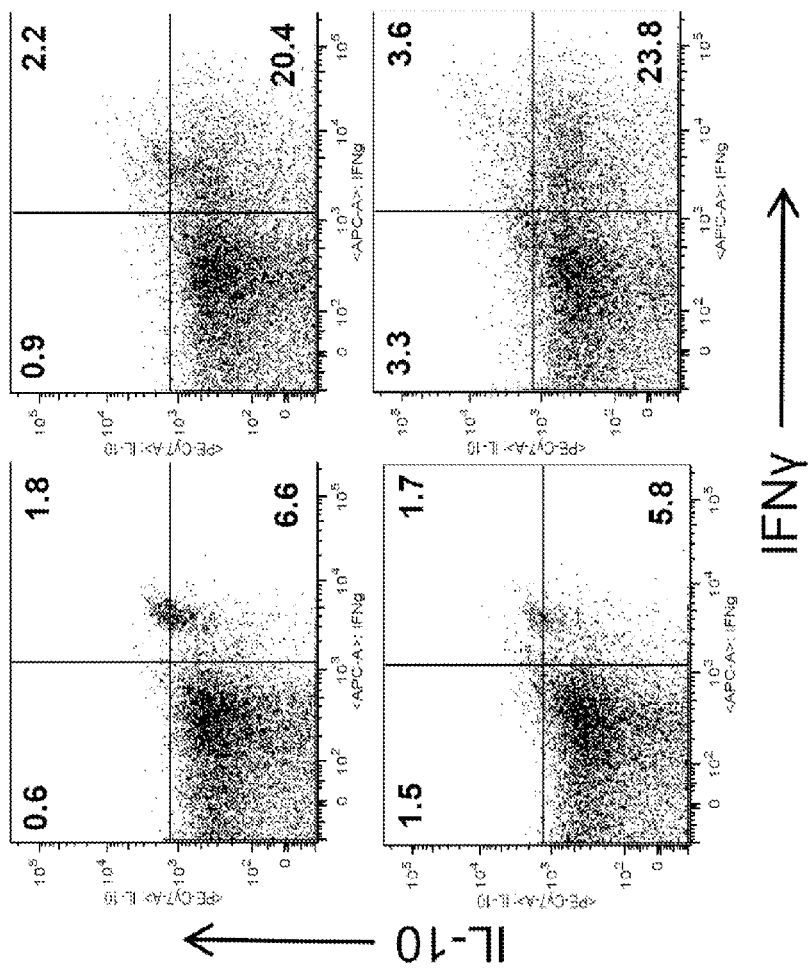

FIGS. 10A-10B are a series of flow cytometry plots demonstrating that intra-tumor injection of (11R)-71-85 inhibits tumor necrosis factor (TNF)-α secretion from tumor-infiltrating T cells. WT C57BL/6 mice were injected with 7.5×10$^5$ PANC02 cells. After 16 days, mice were injected with 80 µg of either (11R)-71-85 or (11R)-Scrambled (Scr) every other day for 1 week. Twenty-four hours after the last intra-tumor injection, tumor infiltrating cells were harvested and restimulated with PMA and ionomycin, or left unstimulated, in the presence of Golgi inhibitor for 4 hours. Expression of cytokines (IL-17A and TNFα—FIG. 10A; IL-10 and IFNγ—FIG. 10B) was determined by flow cytometry.

FIG. 11 is a pair of images showing that intra-tumor injection of (11R)-71-85 reduces tumor vascularization. WT C57BL/6 mice were injected with 7.5×10$^5$ PANC02 cells and 16 days later were injected with 80 µg of either (11R)-71-85 or (11R)-Scrambled. Mice received intra-tumor injections every other day for 2.5 weeks. Twenty-four hours after the last injection, tumors were collected, fixed in formalin, and stained for the endothelial marker CD31, an indicator of tumor vascularization.

Figure 12:
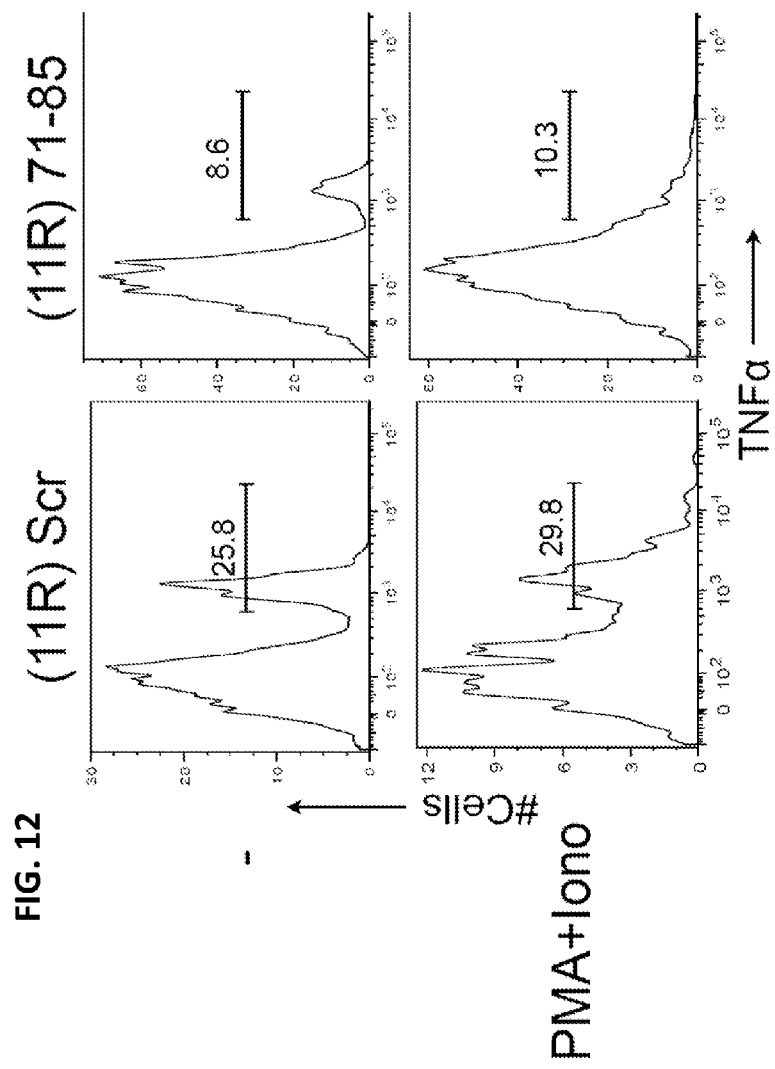

FIG. 12 is a panel of flow cytometry plots showing that intraperitoneal injection of (11R)-71-85 inhibits TNF-α secretion from tumor-infiltrating T cells from KPC mice. KPC mice are genetically engineered to develop pancreatic cancer because of oncogene expression and p53 haploinsufficiency. KPC mice received intraperitoneal injections of 80 µg of either (11R)-71-85 or (11R)-Scrambled every other day for 1 month. Twenty-four hours after the last injection, tumor infiltrating cells were harvested and restimulated with PMA and ionomycin, or left unstimulated, in the presence of Golgi inhibitor for 4 hours. Expression of intracellular TNF-α was determined by flow cytometry.

FIGS. 13A-13D are graphs showing that (11R)-71-85 inhibits PanIN and cancer formation in KPC mice. (FIG. 13A) KPC mice were sub-lethally irradiated at 6 weeks of age and packed with 10×10$^6$ hematopoietic bone marrow cells and the survival was monitored (n=5 per group; *p<0.05, Log-rank test). (FIG. 13B) Quantification of normal ducts and PanIN of KPC mice treated as in (A) (n=6 per group). (FIG. 13C) CD4$^+$ T cells infiltrated in the pancreas were analyzed for TNFα and IFNγ expression by flow cytometry after treatment with (11R) 71-85 or (11R) Scr. Bar graphs show the average percentage of indicated cytokine secreting cells. (n=8 per group; *p<0.05, NS=not significant, unpaired two-tailed Student's t-test). (FIG. 13D) KPC mice were treated as in (A) and the expression of different tumor promoting factors was analyzed in isolated pancreatic epithelial cells by quantitative real-time PCR (n=6 per group).

Figure 14C:
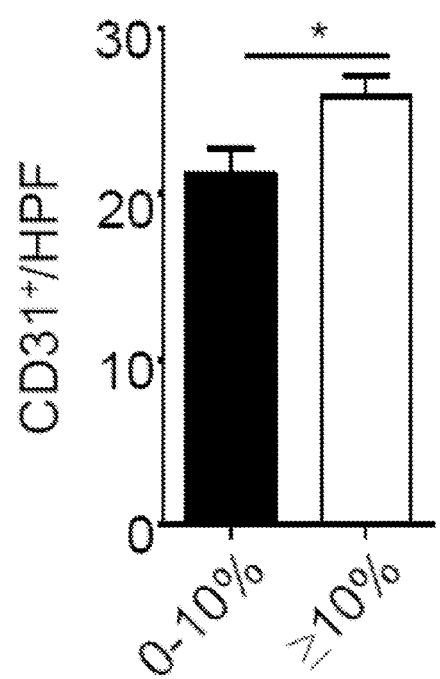

FIGS. 14A-14C are graphs showing higher p38 alternative expression in T cells is associated with shorter survival and tumor neoangiogenesis in human PDAC. (FIG. 14A) Correlation of the patient's survival with lower (0-10%, n=153) versus higher (≥10%, n=40) levels of tumor infiltrating T cells in human pancreas activated by the alternative pathway (Log-rank test). (FIG. 14B) Human PDAC sections were stained for CD3 and the absolute number of CD3+ cells was analyzed per high power field in all samples of lower (0-10%, n=153) and higher (≥10%, n=40) levels of p38 alternatively activated tumor infiltrating T cells (NS=not significant, unpaired two-tailed Student's t-test). (FIG. 14C) Immunohistochemistry with anti-CD31 antibody for the detection of vascular density of patient's samples with lower (0-10%, n=10) versus higher (≥10%, n=10) activation of p38 alternative pathway. (*p<0.05, unpaired two-tailed Student's t-test).

SEQUENCE LISTING

The and amino acid sequences listed in the accompanying sequence listing are shown using standard three letter code for amino acids, as defined in 37 C.F.R. 1.822 The Sequence Listing is submitted as an ASCII text file, created on Apr. 30, 2015, 2.60 KB, which is incorporated by reference herein. In the accompanying sequence listing:

SEQ ID NO: 1 is an amino acid consensus sequence of a Gadd45α polypeptide corresponding to residues 71-85 of Gadd45α.

SEQ ID NO: 2 is the amino acid sequence of residues 71-85 of human Gadd45α.

SEQ ID NO: 3 is the amino acid sequence of residues 71-85 of mouse Gadd45α.

SEQ ID NO: 4 is the amino acid sequence of isoform 1 of the human Gadd45α protein (GenBank Accession No. NP_001915).

DETAILED DESCRIPTION

I. Abbreviations

ATF2 activating transcription factor 2
CIA collagen-induced arthritis
CPP cell-penetrating peptide
EAE experimental autoimmune encephalomyelitis
Gadd45α growth arrest and DNA-damage-inducible alpha
IFN interferon
IL interleukin
IRF interferon regulatory factor
i.v. intravenous
LT lymphotoxin
MAPK mitogen-activated protein kinase
MS multiple sclerosis
NFATc1 nuclear factor of activated T-cells, cytoplasmic, calcineurin-dependent 1
PanIN pancreatic intraepithelial neoplasia precursor lesions
PDAC pancreatic ductal adenocarcinoma
RA rheumatoid arthritis
TCR T cell receptor
TGF transforming growth factor
Th T helper
TIL tumor infiltrating lymphocytes
TNF tumor necrosis factor II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administer: As used herein, administering a composition (e.g. a polypeptide) to a subject means to give, apply or bring the composition into contact with the subject. Administration can be accomplished by any of a number of routes, such as, for example, intravenous, intrathecal, topical, oral, subcutaneous, intramuscular, intraperitoneal, intramuscular or by direct injection into a tissue, such as into a tumor.

Autoimmune disease: A type of disease that arises from inappropriate immune responses targeted against substances or tissues normally present in the body. Autoimmune diseases, include, but are not limited to amyotrophic lateral sclerosis, autoimmune hepatitis, celiac disease, Crohn's disease (inflammatory bowel disease), diabetes type 1, Graves' disease, Guillain-Barre syndrome, Hashimoto's disease, multiple sclerosis, myasthenia gravis, psoriasis, rheumatoid arthritis, Sjögren's syndrome, systemic lupus erythematosis, and ulcerative colitis.

Clinical outcome: Refers to the health status of a patient following treatment for a disease or disorder (such as pancreatic cancer), or in the absence of treatment. Clinical outcomes include, but are not limited to, a decrease in incidence of cancer, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Cell-penetrating peptide (CPP): Peptides that facilitate the cellular uptake of another protein or molecular cargo linked by a covalent bond or non-covalent interaction. CPPs generally deliver cargo into a cell by endocytosis. In many instances, CPPs have an amino acid composition that is rich in charged amino acids, such as lysine or arginine, or have sequences that contain an alternating pattern of polar/charged amino acids and non-polar/hydrophobic amino acids.

Collagen-induced arthritis (CIA) model: The most commonly used autoimmune model of rheumatoid arthritis. This model can be used to study disease pathogenesis and to validate therapeutic agents. Autoimmune arthritis is induced in this model by immunization with an emulsion of complete Freund's adjuvant and type II collagen (CII). Protocols for handling and preparation of CII, as well as selection of mouse strains, proper immunization technique and evaluation of the arthritis incidence and severity are known in the art (see, for example, Brand et al., *Nat Protoc* 2(5):1269-1275, 2007). Typically, the first signs of arthritis appear in this model 21-28 days after immunization. The chief pathological features of CIA include a proliferative synovitis with infiltration of polymorphonuclear and mononuclear cells, pannus formation, cartilage degradation, erosion of bone, and fibrosis. As in rheumatoid arthritis in humans, pro-inflammatory cytokines, such as TNF-α and IL-1β, are abundantly expressed in the arthritic joints of mice with CIA, and blockade of these molecules results in a reduction of disease severity.

Contacting: Placement in direct physical association; includes both in solid and liquid form.

Decrease in survival: As used herein, "decrease in survival" refers to a decrease in the length of time before death of a patient, or an increase in the risk of death for the patient. A decrease in survival also can refer to a decrease in the average time to death in a group, such as a group of patients diagnosed with pancreatic cancer.

Differentiation: Refers to the process by which a cell develops into a specific type of cell. For example, a T cell can develop into a specific T cell subtype, such as Th1, Th2, Th17, T regulatory cell or cytotoxic T cell. The differentiation of T cells into specific T helper subtypes is influenced by the cytokine environment (e.g., IFN-γ and IL-12 promote Th1 differentiation; IL-4 promotes Th2 differentiation; and TGF-β, IL-6, IL-21 and IL-23 promote Th17 differentiation).

Experimental autoimmune encephalomyelitis (EAE): An animal model of MS (for example, see Gold et al., *Brain* 129:1953-1971, 2006). EAE animals exhibit characteristic plaques of tissue injury disseminated throughout the central nervous system. Plaques show infiltration of nervous tissue by lymphocytes, plasma cells, and macrophages, which cause destruction of the myelin sheaths that surround nerve cell axons in the brain and spinal cord. In some cases, EAE is induced by immunization of susceptible animals, such as mice, rats, guinea pigs, or non-human primates, with either myelin or various components of myelin. For example, EAE can be induced by immunization with components of the myelin sheath, such as myelin basic protein, proteolipid protein, or myelin oligodendrocyte glycoprotein (MOG). EAE is a useful and widely accepted model for studying mechanisms of autoimmune CNS tissue injury and for testing potential therapies for MS. EAE also includes "passive EAE" which is induced in the same manner in donor animals, but involves the transfer of activated T-cells harvested from the donor animal's lymph nodes to naïve recipient animals.

Fusion protein: A protein containing amino acid sequence from at least two different (heterologous) proteins or peptides. In some examples herein, the fusion protein comprises a portion of Gadd45α and a cell-penetrating peptide. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Growth arrest and DNA-damage-inducible alpha (Gadd45α): A member of a group of genes whose transcript levels are increased following stressful growth conditions and treatment with DNA-damaging agents. The Gadd45α protein responds to environmental stresses by mediating activation of the p38/JNK pathway via MTK1/MEKK4 kinase. Gadd45α has previously been shown to inhibit the alternative p38 activation pathway in T cells and the absence of Gadd45α results in T cell hyperproliferation and autoimmunity (Salvador et al., *Nat Immunol* 6(4):396-402, 2005). Nucleotide and amino acid sequences for Gadd45α are publically available, such as in the NCBI database (for example under Gene ID 1647 for human Gadd45α). An exemplary sequence for human Gadd45α is set forth herein as SEQ ID NO: 4.

Heterologous: A heterologous protein or polypeptide refers to a protein or polypeptide derived from a different source or species.

Inflammatory disease or disorder: Any disease, disorder or condition that is characterized by the presence of inflammation (i.e. redness, heat, swelling and/or pain resulting from infection, injury, tissue damage, irritation etc.). Examples of inflammatory diseases include, but are not limited to autoimmune diseases (e.g. inflammatory bowel disease, rheumatoid arthritis and celiac disease), asthma, vasculitis, chronic prostatitis, pelvic inflammatory disease, cancer, atherosclerosis, ischemic heart disease, reperfusion injury, transplant rejection, sarcoidosis, allergic hypersensitivity and glomerulonephritis.

Mitogen-activated protein kinase (MAPK) pathway: A cellular signaling pathway that regulates cellular processes such as proliferation, survival, and migration. Mammals express at least four distinctly regulated groups of MAPKs, extracellular signal-related kinases (ERK)-1/2, Jun amino-terminal kinases (JNK1/2/3), p38 proteins (p38alpha/beta/gamma/delta) and ERK5, which are activated by specific MAPKKs: MEK1/2 for ERK1/2, MKK3/6 for the p38, MKK4/7 (JNKK1/2) for the JNKs, and MEK5 for ERK5. Each MAPKK can be activated by more than one MAPKKK, increasing the complexity and diversity of MAPK signaling. Each MAPK pathway contains a three-tiered kinase cascade comprising a MAP kinase kinase kinase (MAPKKK, MAP3K, MEKK or MKKK), a MAP kinase kinase (MAPKK, MAP2K, MEK or MKK) and the MAPK. This three-tier module mediates ultrasensitive switch-like responses to stimuli.

MAPK family: A family of serine/threonine protein kinases involved in directing cellular responses to a diverse array of stimuli, including mitogens, osmotic stress, heat shock and proinflammatory cytokines. MAPKs regulate, for example, proliferation, gene expression, differentiation, mitosis, cell survival and apoptosis. Members of the MAPK/ERK family include, but are not limited to MAPK1 (ERK2), MAPK3 (ERK1), MAPK4 (ERK4), MAPK6 (ERK3), MAPK7 (ERK5), MAPK8 (JNK1), MAPK9 (JNK2), MAPK10 (JNK3), MAPK11 (p38-β), MAPK12 (p38-γ), MAPK13 (p38-δ) and MAPK14 (p38-α).

Metastasis: Refers to the spread of cancer cells from the original tumor to other sites in the body.

Multiple sclerosis: An autoimmune disease classically described as a central nervous system white matter disorder disseminated in time and space that presents as relapsing-remitting illness in 80-85% of patients. Diagnosis can be made by brain and spinal cord magnetic resonance imaging (MRI), analysis of somatosensory evoked potentials, and analysis of cerebrospinal fluid to detect increased amounts of immunoglobulin or oligoclonal bands. MRI is a particularly sensitive diagnostic tool. MRI abnormalities indicating the presence or progression of MS include hyperintense white matter signals on T2-weighted and fluid attenuated inversion recovery images, gadolinium enhancement of active lesions, hypointensive "black holes" (representing gliosis and axonal pathology), and brain atrophy on T1-weighted studies. Serial MRI studies can be used to indicate disease progression. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary progressive multiple sclerosis (PPMS) presents initially in the progressive form.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

p38 mitogen-activated protein kinases: A class of MAPKs that are responsive to cellular stresses, such as inflammatory cytokines, ultraviolet radiation, lipopolysaccharide, heat shock, osmotic shock and growth factors. p38 proteins are involved in a number of cellular processes, including cell differentiation, apoptosis and autophagy. Four p38 MAPKs have been identified—p38-α (MAPK14), p38-β (MAPK11), p38-γ (MAPK12) and p38-δ (MAPK13); of these, p38α, p38β and p38δ are expressed in T cells. As used herein, "p38" refers to any of the p38 proteins (p38α, p38β, p38γ and p38δ). In particular embodiments, "p38" refers to any p38 protein expressed in T cells, including p38α, p38β and p38δ.

Pancreatic cancer: A disease in which malignant (cancer) cells are found in the tissues of the pancreas. Also called exocrine cancer.

Pancreatic ductal adenocarcinoma (PDAC): The most common type of pancreatic malignancy. PDAC is the fourth leading cause of cancer death in the United States with a mean survival of less than six months. This type of cancer is capable of rapid dissemination to the lymphatic system and distant organs. PDAC is distinct from other cancers due to the biological barrier the tumor builds around itself. Patients whose disease is caught at an early stage have a better chance of long-term survival, but the pancreas emits few known clues to signal that the carcinogenic process has begun. Therefore, there are currently no early detection tests.

Pharmaceutically acceptable carriers: The pharmaceutically acceptable carriers useful in the methods disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of polypeptides.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

Poly-arginine or poly-lysine: A polymer of multiple arginine or lysine residues, respectively. In the context of the present disclosure, "poly-arginine" or "poly-lysine" includes peptides made up of about 4 to about 20 arginine or lysine residues, such as about 4, 5, 6, 7, 8, 9, 10, 11, 12, 13, 14, 15, 16, 17, 18, 19 or 20 arginine or lysine residues, respectively. In particular embodiments herein, the poly-arginine peptide includes 6 to 12 arginine residues, or the poly-lysine peptide includes 6 to 12 lysine residues. In one non-limiting example, the poly-arginine peptide consists of 11 arginine (11R) residues.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

A conservative substitution in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease, such as a T-cell and/or p38-mediated disease or disorder.

Prognosis: The likelihood of the clinical outcome for a subject afflicted with a specific disease or disorder, such as pancreatic cancer. With regard to cancer, the prognosis is a representation of the likelihood (probability) that the subject will survive (such as for one, two, three, four or five years) and/or respond to anti-cancer treatment, and/or the likelihood (probability) that the tumor will metastasize. In some embodiments, a "poor prognosis" indicates a greater than 50% chance that the subject will not survive to a specified time point (such as one, two, three, four or five years), and/or a greater than 50% chance that the tumor will metastasize. In several examples, a poor prognosis indicates that there is a greater than 60%, 70%, 80%, or 90% chance that the subject will not survive and/or a greater than 60%, 70%, 80% or 90% chance that the tumor will metastasize. Conversely, a "good prognosis" indicates a greater than 50% chance that the subject will survive to a specified time point (such as one, two, three, four or five years), and/or a greater than 50% chance that the tumor will not metastasize. In several examples, a good prognosis indicates that there is a greater than 60%, 70%, 80%, or 90% chance that the subject will survive and/or a greater than 60%, 70%, 80% or 90% chance that the tumor will not metastasize.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered solely by addition, substitution, or deletion of a portion of a natural nucleic acid molecule or protein.

Rheumatoid arthritis: A systemic autoimmune disorder characterized by chronic inflammation of the joints. This disease can also include inflammation of tissues in other areas of the body, such as the lungs, heart and eyes.

Sample (or biological sample): A biological specimen containing genomic DNA, RNA, protein, or combinations thereof, obtained from a subject. Examples include, but are not limited to, peripheral blood, urine, saliva, tissue biopsy (such as pancreatic tissue), surgical specimen, and autopsy material. In one example, a sample includes a biopsy of a pancreatic tumor or a sample of normal tissue, such as pancreatic tissue (from a subject not afflicted with a known disease or disorder, such as a cancer-free subject).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Subject: A human or non-human animal. In one embodiment, the subject has a T cell- or p38-mediated disorder.

Synthetic: Produced by artificial means in a laboratory, for example a synthetic polypeptide can be chemically synthesized in a laboratory.

T cell- or p38-mediated disorder: Any disease, disorder or condition that is associated with aberrant or pathological activation of T cells and/or the alternative p38 activation pathway in T cells. T cell- or p38-mediated disorders include, for example, autoimmune disorders (such as, but not limited to multiple sclerosis, rheumatoid arthritis and inflammatory bowel disease) and inflammatory disorders, including tumors that are associated with local inflammatory responses (e.g. pancreatic cancer).

T cell receptor (TCR): A molecule expressed on the surface of T lymphocytes that is responsible for recognizing antigens bound to major histocompatibility complex (MHC) molecules. The TCR is a heterodimer consisting of either an alpha ($\alpha$) and beta ($\beta$) chains, or gamma ($\gamma$) and delta ($\delta$) chains. In mammals, the TCR is expressed as part of a complex with four CD3 chains ($\gamma$, $\delta$, and 2$\epsilon$ chains) and the $\zeta$ chain.

T helper (Th) cells: A type of T cell that activates or directs other immune cells but has no intrinsic cytotoxic of phagocytic activity. Th cells play essential roles in B cell antibody class switching, activation and growth of cytotoxic T cells and bactericidal activity of phagocytic cells. Th1 and Th2 cells are subsets of Th cells that primarily interact with macrophages and B cells, respectively. Th1 cells produce interferon (IFN)-$\gamma$, interleukin (IL)-2, lymphotoxin (LT)-$\alpha$ and transforming growth factor (TGF)-$\beta$, and function to maximize the killing efficiency of macrophages and the proliferation of cytotoxic CD8$^+$ T cells. Th2 cells produce IL-4, IL-5, IL-6, IL-13 and IL-25, and function by stimulating B cell proliferation, inducing B cell class switching and increasing neutralizing antibody production. Th17 cells are another subset of T helper cells that produce the effector cytokines IL-17, IL-21 and IL-22. Th17 cells are considered developmentally distinct from Th1 and Th2 cells. Excessive numbers of Th17 cells are thought to play a role in several autoimmune diseases. TGF-β, IL-6, IL-21, and IL-23 have been associated with the differentiation of T cells to Th17 cells.

Therapeutically effective amount: A dose sufficient to prevent advancement of a disease, or to cause regression of the disease, or which is capable of reducing symptoms caused by the disease, such as a T cell- or p38-mediated disorder (e.g., an autoimmune disease, such as multiple sclerosis or rheumatoid arthritis, or inflammatory disorder, such as cancer).

Tumor vascularization: The formation of new blood vessels and/or growth of existing blood vessels in a tumor.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Gadd45α Polypeptides, Fusion Proteins and Compositions

Disclosed herein is the identification of a minimal region of the growth arrest and DNA damage-inducible alpha (Gadd45α) protein that is required for binding to p38 and inhibiting the alternative p38 activation pathway in T cells. In particular, the Gadd45α polypeptides disclosed herein are capable of inhibiting the enzymatic activity of tyrosine 323-phosphorylated p38, inhibiting T cell proliferation in response to TCR activation (but not in response to stimuli that activate the classical p38 activation pathway), inhibiting skewing of T cells to Th1 and Th17 cells and reducing proinflammatory cytokine production. Moreover, administration of the disclosed Gadd45α polypeptides inhibits activation of the T-cell specific alternative p38 activation pathway in vivo and significantly reduces tumor formation and growth of inflammatory pancreatic tumors.

Provided herein are Gadd45α polypeptides capable of inhibiting the T-cell specific alternative p38 activation pathway. In some embodiments, the Gadd45α polypeptide is no more than 25 amino acids in length, or no more than 20 amino acids in length, and comprises residues 71-85 of Gadd45α. In some embodiments, the Gadd45α is human or mouse Gadd45α. In some examples, the amino acid sequence of the Gadd45α polypeptide comprises LQIHFTLIXAFCCEN (SEQ ID NO: 1), wherein X is Q or R. In particular examples, the Gadd45α polypeptide comprises or consists of the amino acid sequence LQIHFTLIQAFCCEN (SEQ ID NO: 2) or LQIHFTLIRAFCCEN (SEQ ID NO: 3). In some instances, the Gadd45α polypeptide contains 1 to 5, such as 1, 2, 3, 4 or 5 conservative amino acids substitutions in the polypeptide sequence LQIHFTLIQAFCCEN (SEQ ID NO: 2) or LQIHFTLIRAFCCEN (SEQ ID NO: 3). Conservative amino acid substitutions are well known in the art and exemplary substitutions are described herein (see Terms and Methods). In some embodiments, the Gadd45α polypeptide is a synthetic or recombinant (i.e. non-naturally occurring) polypeptide.

Also provided herein are fusion proteins comprising a Gadd45α polypeptide and a heterologous protein or peptide. In some embodiments, the heterologous peptide is a peptide that promotes cellular uptake of the fusion protein, such as a cell-penetrating peptide (CPP).

CPPs are a family of polypeptides that facilitate transduction of proteins, nucleic acids or other compounds across membranes in a receptor-independent manner (Wadia and Dowdy, Curr. Protein Pept. Sci. 4(2):97-104, 2003). Typically, CPPs are short polycationic sequences that can facilitate cellular uptake of compounds to which they are linked into endosomes of cells.

The capacity of certain peptides to deliver proteins or nucleic acids into cells was originally described for the HIV-encoded Tat protein, which was shown to cross membranes and initiate transcription. It was then discovered that the portion of the Tat protein that was required for the transduction of the protein was only an 11 amino acid polypeptide, referred to as the Tat peptide. When fused with other proteins, the Tat peptide has been demonstrated to deliver these proteins, varying in size from 15 to 120 kDa, into cells in tissue culture (Frankel and Pabo, Cell 55(6):1189-93, 1988; Green and Loewenstein, J. Gen. Microbiol. 134(3):849-55, 1988; Vives et al., J. Biol. Chem. 272(25):16010-7, 1997; Yoon et al., J. Microbiol. 42(4):328-35, 2004; Cai et al., Eur. J. Pharm. Sci. 27(4):311-9, 2006).

Other known CPPs include PENETRATIN™, a 16 amino acid peptide derived from the third helix of the Drosophila Antennapedia homeobox gene (U.S. Pat. No. 5,888,762; Derossi et al., J. Biol. Chem. 269:10444-10450, 1994; Schwarze et al., Trends Pharmacol. Sci. 21:45-48, 2000); transportan, a 27 amino acid chimeric peptide comprised of 12 amino acids from the N-terminus of the neuropeptide galanin and the 14-amino acid protein mastoparan, connected via a lysine (U.S. Pat. No. 6,821,948; Pooga, FASEB J. 12:67-77, 1998; Hawiger, Curr. Opin. Chem. Biol. 3:89-94, 1999); peptides from the VP22 protein of herpes simplex virus (HSV) type 1 (Elliott et al., Cell 88:223-233, 1997); the UL-56 protein of HSV-2 (U.S. Pre-Grant Publication No. 2006/0099677); and the Vpr protein of HIV-1 (U.S. Pre-Grant Publication No. 2005/0287648). In addition, a number of artificial peptides also are known to function as CPPs, such as poly-arginine, poly-lysine and others (see, for example, U.S. Application Publication Nos. 2006/0106197; 2006/0024331; 2005/0287648; and 2003/0125242; Zhibao et al., Mol. Ther. 2:339-347, 2000; and Laus et al. Nature Biotechnol. 18:1269-1272, 2000).

In some examples, the CPP is rich in charged amino acids, such as lysine or arginine. In other examples, the CPP contains an alternating pattern of polar/charged amino acids and non-polar/hydrophobic amino acids. In particular non-limiting examples, the CPP comprises poly-arginine, such as 6, 7, 8, 9, 10, 11 or 12 arginine residues. In one example, poly-arginine comprises or consists of 11 arginine (11R) residues. In other non-limiting examples, the CPP comprises poly-lysine, such as 6, 7, 8, 9, 10, 11 or 12 lysine residues.

In other embodiments, the heterologous protein or peptide is a protein tag, such as an affinity tag (for example, chitin binding protein, maltose binding protein, glutathione-S-transferase or poly-His), an epitope tag (for example, V5, c-myc, HA or FLAG) or a fluorescent tag (e.g., GFP or another well-known fluorescent protein).

In one embodiment, the fusion protein comprises 11R fused to the N-terminus of a Gadd45α polypeptide. In some examples, the fusion protein comprises or consists of 11R fused to the amino acid sequence LQIHFTLIQAFCCEN (SEQ ID NO: 2) or LQIHFTLIRAFCCEN (SEQ ID NO: 3).

Further provided herein are compositions comprising a Gadd45α polypeptide or Gadd45α fusion protein disclosed herein. In some embodiments, the composition further comprises a pharmaceutically acceptable carrier.

IV. Use of Gadd45α Polypeptides

It is disclosed herein that Gadd45α polypeptides comprising a minimal region that interacts with p38 (Gadd45α residues 71-85) are capable of inhibiting activation of the T-cell specific alternative p38 activation pathway in vitro, ex vivo and in vivo. In particular, the Gadd45α polypeptides disclosed herein inhibit T cell proliferation in response to TCR activation, inhibit skewing of T cells to Th1 and Th17 cells and reduce proinflammatory cytokine production. It is also demonstrated herein that administration of the disclosed Gadd45α polypeptides significantly reduces tumor formation and growth of inflammatory pancreatic tumors. Furthermore, data disclosed herein demonstrates that detection of tumor-infiltrating T cells positive for tyrosine 323-phsophorylated p38 can be used to determine the prognosis of a patient diagnosed with pancreatic ductal adenocarcinoma (PDAC).

Provided herein is a method of inhibiting proliferation of T cells, such as inhibiting proliferation of T cells in response to TCR stimulation. In some embodiments, the method includes contacting the T cells with a Gadd45α polypeptide, fusion protein or composition disclosed herein, thereby inhibiting proliferation of the T cells. In some examples, the method of inhibiting proliferation of T cells is an ex vivo method in which T cells have been isolated from a subject and the isolated T cells are contacted with the Gadd45α polypeptide, fusion protein or composition. In other examples, the method of inhibiting proliferation of T cells is an in vivo method that includes administering the Gadd45α polypeptide, fusion protein or composition to the subject. In particular examples, the subject exhibits aberrant proliferation of T cells and/or aberrant activation of the alternative p38 pathway. For example, the subject can be a subject suffering from an autoimmune or inflammatory disease or disorder, such as multiple sclerosis, rheumatoid arthritis or cancer, such as pancreatic cancer (e.g. PDAC).

In some examples, T cell proliferation is inhibited at least 10%, at least 20%, at least 30%, at least 40%, at least 50%, at least 60%, at least 70% or at least 80% compared to a control (e.g. untreated T cells). Methods for detecting and quantifying proliferation of T cells is well known in the art, including, for example, measuring [$^3$H]-thymidine incorporation or measuring T cell populations using fluorescence activated cell sorting based on T cell-specific markers.

Further provided is a method of inhibiting differentiation of T cells into Th1 or Th17 cells. In some embodiments, the method includes contacting the T cells with a Gadd45α polypeptide, fusion protein or composition disclosed herein, thereby inhibiting differentiation of the T cells. In some examples, the method of inhibiting differentiation of T cells is an ex vivo method in which T cells have been isolated from a subject and the isolated T cells are contacted with the Gadd45α polypeptide, fusion protein or composition. In other examples, the method of inhibiting differentiation of T cells is an in vivo method that includes administering the Gadd45α polypeptide, fusion protein or composition to a subject. In particular examples, the subject is a subject having a T cell- and/or p38-mediated autoimmune or inflammatory disorder, such as multiple sclerosis, rheumatoid arthritis or cancer (e.g. pancreatic cancer).

In some examples, differentiation of T cells into Th1 or Th17 cells is inhibited at least 10%, at least 20%, at least 30%, at least 40%, at least 50%, at least 60%, at least 70% or at least 80% relative to a control (e.g. untreated T cells). Methods for evaluating differentiation of T cells into particular T helper (Th) subtypes are well known in the art, including the methods described in the Examples. For instance, Th subtypes can be determined by evaluating cytokine expression profiles or subtype-specific transcription factor expression. Th1 cells are characterized by expression of the cytokines including IFN-γ, IL-2 and LT-α, and the transcription factor T-bet; Th2 cells typically produce IL-4, IL-5, IL6 and IL-13; and Th17 cells primarily express IL-17, IL-21 and IL-22 (Zhu and Paul, *Blood* 112(5):1557-1568, 2008).

Also provided herein is a method of treating a subject having a T cell- and/or p38-mediated autoimmune or inflammatory disorder. In some embodiments, the method includes selecting a subject with a T cell- and/or p38-mediated autoimmune or inflammatory disorder and administering to the subject a therapeutically effective amount of a Gadd45α polypeptide, fusion protein or composition disclosed herein, thereby treating the subject. The T cell- and/or p38-mediated autoimmune or inflammatory disorder is any disease, disorder or condition that is associated with aberrant or pathological activation of T cells and/or the alternative p38 activation pathway in T cells. In some embodiments, the T cell- and/or p38-mediated disorder is an autoimmune disorder, such as, but not limited to amyotrophic lateral sclerosis, autoimmune hepatitis, celiac disease, Crohn's disease (inflammatory bowel disease), diabetes type 1, Graves' disease, Guillain-Barre syndrome, Hashimoto's disease, multiple sclerosis, myasthenia gravis, psoriasis, rheumatoid arthritis, Sjögren's syndrome, systemic lupus erythematosis, and ulcerative colitis. In other embodiments, the T cell- and/or p38-mediated disorder is an inflammatory disorder, such as but not limited to asthma, vasculitis, chronic prostatitis, pelvic inflammatory disease, cancer, atherosclerosis, ischemic heart disease, reperfusion injury, transplant rejection, sarcoidosis, allergic hypersensitivity and glomerulonephritis. In some examples, the T cell- and/or p38-mediated autoimmune or inflammatory disorder comprises multiple sclerosis, rheumatoid arthritis, inflammatory bowel disease or pancreatic cancer (such as, but not limited to, PDAC).

Further provided herein is a method of inhibiting tumor vascularization in a subject. In some embodiments, the method includes selecting a subject with a tumor and administering to the subject a therapeutically effective amount of a Gadd45α polypeptide, fusion protein or composition disclosed herein. In some examples, the tumor is a pancreatic tumor, such as a PDAC tumor. In some examples, administration comprises intra-tumor injection. In non-limiting examples, tumor vascularization is inhibited at least 10%, at least 20%, at least 30%, at least 40%, at least 50%, at least 60%, at least 70% or at least 80% relative to a control. Methods of detecting and evaluating tumor vascularization are known in the art. For example, tumor vascularization can be evaluated by staining tumor cells for an endothelial marker, such as CD31 or CD34.

Methods of administering therapeutic proteins are well known in the art, and include both systemic and local administration. In some embodiments, the Gadd45α polypeptide, fusion protein or composition is administered intravenously or intraperitoneally. In some examples in which the subject has a tumor, the Gadd45α polypeptide, fusion protein or composition is administered directly into the tumor. Single or multiple administrations (such as 2, 3, 4, 5 or more administrations) can be utilized depending on, for example, the type and severity of disease to be treated, and the general health of the subject.

The amount of a Gadd45α polypeptide, fusion protein or composition administered to a subject is generally an amount sufficient to at least partially inhibit activation of p38 and/or treat or ameliorate one or more signs or symptoms of disease. A therapeutically effective amount of a Gadd45α polypeptide, fusion protein or composition can be determined by a medical practitioner. In some embodiments, the therapeutically effective amount of a Gadd45α polypeptide, fusion protein or composition disclosed herein is an amount that provides either subjective relief of one or more symptoms or an objectively identifiable improvement as noted by the clinician or other qualified observer. In some examples, the Gadd45α polypeptide or fusion protein is administered at a dose of about 20 to about 100 µg, such as about 20, about 25, about 30, about 35, about 40, about 45, about 50, about 55, about 60, about 65, about 70, about 80, about 90 or about 100 µg.

Also provided herein is a method of determining the prognosis of a subject diagnosed with PDAC by calculating the percentage of tumor-infiltrating T cells positive for tyrosine 323-phosphorylated p38 (p38 pY323) in a tumor sample obtained from the subject; and determining that the subject has a poor prognosis if at least 10% of the T cells are positive for p38 pY323.

A poor prognosis refers to any negative clinical outcome. For example, in some embodiments, a poor prognosis is a decrease in the time of survival. In some embodiments, a poor prognosis is an increase in the likelihood of metastasis of the cancer. In other embodiments, a poor prognosis refers to failure to respond to therapy, such as radiation therapy or chemotherapy. In particular embodiments, the poor prognosis is a decrease in time of survival. In some examples, a poor prognosis indicates that the subject is likely to survive less than one year.

Methods for detecting tyrosine 323-phosphorylated p38 in a tumor sample are well known in the art, and include, for example, immunohistochemical detection using an antibody specific for tyrosine 323-phosphorylated p38 (see Example 5 below).

V. Additional Embodiments

1. An isolated growth arrest and DNA-damage-inducible alpha (Gadd45α) polypeptide no more than 25 amino acids in length, wherein the amino acid sequence of the polypeptide comprises LQIHFTLIXAFCCEN (SEQ ID NO: 1), wherein X is Q or R.

2. The isolated Gadd45α polypeptide of 1 which is no more than 20 amino acids in length.

3. The isolated Gadd45α polypeptide of 1 or 2, comprising the amino acid sequence LQIHFTLIQAFCCEN (SEQ ID NO: 2) or LQIHFTLIRAFCCEN (SEQ ID NO: 3).

4. The isolated Gadd45α polypeptide of 1 or 2, consisting of the amino acid sequence LQIHFTLIQAFCCEN (SEQ ID NO: 2) or LQIHFTLIRAFCCEN (SEQ ID NO: 3).

5. A fusion protein comprising the Gadd45α polypeptide of any one of 1-4 and a heterologous peptide.

6. The fusion protein of 5, wherein the heterologous peptide is a cell-penetrating peptide (CPP).

7. The fusion protein of 6, wherein the CPP comprises poly-arginine.

8. The fusion protein of 7, wherein poly-arginine comprises or consists of 11 arginine (11R) residues.

9. The fusion protein of 8, consisting of 11R fused to the N-terminus of the Gadd45α polypeptide.

10. The fusion protein of 8, consisting of 11R fused to the amino acid sequence LQIHFTLIQAFCCEN (SEQ ID NO: 2) or LQIHFTLIRAFCCEN (SEQ ID NO: 3).

11. A composition comprising the polypeptide or fusion protein of any one of 1-10 and a pharmaceutically acceptable carrier.

12. An in vitro or in vivo method of inhibiting proliferation of T cells in response to T cell receptor stimulation, or of inhibiting differentiation of T cells into Th1 or Th17 cells, comprising contacting the T cells with the polypeptide, fusion protein or composition of any one of 1-11, thereby inhibiting proliferation of the T cells.

13. The method of 12 which is an ex vivo method, wherein the T cells have been isolated from a subject and the isolated T cells are contacted with the polypeptide or fusion protein.

14. A method of inhibiting proliferation of T cells in response to T cell receptor stimulation, or of inhibiting differentiation of T cells into Th1 or Th17 cells, in a subject comprising administering the polypeptide, fusion protein or composition of any one of 1-11 to the subject.

15. A method of treating a subject with a T cell- and/or p38-mediated autoimmune or inflammatory disorder, comprising selecting a subject with a T cell- and/or p38-mediated autoimmune or inflammatory disorder and administering to the subject a therapeutically effective amount of the polypeptide, fusion protein or composition of any one of 1-11, thereby treating the subject.

16. The method of 16, wherein the T cell- and/or p38-mediated autoimmune or inflammatory disorder comprises multiple sclerosis, rheumatoid arthritis or pancreatic cancer.

17. The method of 15 or 16, wherein administration comprises intravenous, intra-tumor or intraperitoneal administration.

18. The method of 17, wherein the T cell- and/or p38-mediated autoimmune or inflammatory disorder comprises pancreatic cancer and administration comprises intra-tumor injection.

19. A method of inhibiting tumor vascularization in a subject, comprising selecting a subject with a tumor and administering to the subject a therapeutically effective amount of the polypeptide, fusion protein or composition of any one of 1-11, thereby inhibiting tumor vascularization in the subject.

20. The method of 19, wherein the tumor is a pancreatic tumor.

21. The method of 19 or 20, wherein administration comprises intra-tumor administration.

22. The method of 19, wherein the polypeptide or fusion protein is administered at a dose of about 20 to about 100 µg.

23. The method of 14, wherein the polypeptide or fusion protein is administered at a dose of about 20 to about 100 µg.

24. The method of 15, wherein the polypeptide or fusion protein is administered at a dose of about 20 to about 100 µg.

25. A method of determining the prognosis of a subject diagnosed with pancreatic ductal adenocarcinoma (PDAC), comprising:
calculating the percentage of tumor-infiltrating T cells positive for tyrosine 323-phosphorylated p38 (p38 pY323) in a tumor sample obtained from the subject; and
determining that the subject has a poor prognosis if at least 10% of the T cells are positive for p38 pY323.

26. The method of 25, wherein the poor prognosis is a decrease in time of survival.

The following examples are provided to illustrate certain particular features and/or embodiments. These examples should not be construed to limit the disclosure to the particular features or embodiments described.

EXAMPLES

Example 1

In Vitro Inhibition of the Alternative p38 Activation Pathway by a Gadd45α Polypeptide This example describes a Gadd45α 71-85 polypeptide fused to a cell-penetrating peptide (11R) and its ability to block the T cell-specific alternative p38 activation pathway. The minimal region of Gadd45α capable of binding to p38 was identified by fusing various truncated portions of Gadd45α to GST and using the product to pull down recombinant p38α in vitro. The 71-85 fragment pulled down p38α as well as the full length protein. Furthermore, deletion of 71-80 from the full length Gadd45α rendered it incapable of pulling down p38α.

(11R)-71-85

Figure 1:
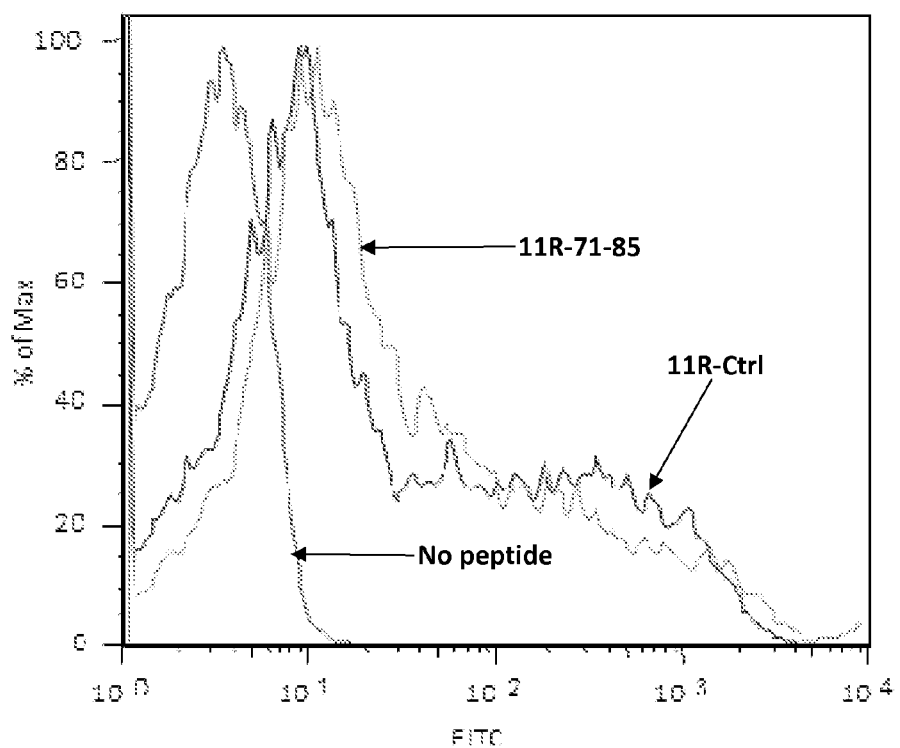
FIG. 1 is a graph showing cellular uptake of (11R)-71-85 and (11R)-Ctrl. Purified CD4$^+$ T cells were treated with either FITC conjugated (11R)-71-85 or (11R)-Ctrl, or left untreated for 2 hours at 37° C. After incubation, cells were washed and analyzed by flow cytometry for FITC positivity.

To generate a cell-permeable form of the Gadd45α 71-85 peptide, 11 arginine residues were added to the N-terminus to produce a fusion protein referred to herein as (11R)-71-85. Cell-permeability of (11R)-71-85 was tested using purified CD4$^+$ T cells. (11R)-71-85 and a control peptide fused to 11 arginine residues (referred to as (11R)-Ctrl) were FITC conjugated. Purified CD4$^+$ T cells were treated with either FITC conjugated (11R)-71-85 or (11R)-Ctrl, or left untreated for 2 hours at 37° C. After incubation, cells were washed and analyzed by flow cytometry for FITC positivity. As shown in FIG. 1, both 11R-conjugated peptides were taken up by the T cells.

In Vitro Inhibition of the p38 Alternative Pathway

To test whether (11R)-71-85 can inhibit the alternative p38 activation pathway in vitro, an assay was performed to detect phosphorylation of activating transcription factor 2 (ATF2), a target of activated p38, in the presence and absence of (11R)-71-85. Purified p38 proteins were activated by incubation with active Zap70 in kinase buffer for 1 hour. (11R)-71-85 (0.2, 0.5, 1.0, 2.0 or 4.0 μg) or (11R)-Ctrl (4.0 μg) was then added and incubated for 30 minutes at 30° C. One μg ATF2 and 10 μCi [$^{32}$P]ATP were added and incubated for 45 minutes at 30° C. Phosphorylated products were resolved by SDS-PAGE, transferred to nitrocellulose membranes, and visualized by phosphorimager. As shown in FIG. 2, incubation with (11R)-71-85, but not (11R)-Ctrl, led to a decrease in phosphorylation of ATF2. In addition, the decrease in ATF2 phosphorylation was dependent on the dose of (11R)-71-85. These results demonstrate that (11R)-71-85 is capable of inhibiting the alternative p38 activation pathway.

Inhibition of T Cell Proliferation and Inflammatory Cytokine Production

The ability of (11R)-71-85 to inhibit T cell proliferation and inflammatory cytokine production was also evaluated. T cells were purified from spleen and treated with different concentrations (0.2, 0.5, 1.0, 2.0 or 4.0 μg) of (11R)-71-85 or the control peptide (11R)-Ctrl. Cells were then washed and stimulated with anti-CD3 and anti-CD28 for 2 days and finally pulsed with 1 μCi [$^3$H]-thymidine 14 hours before harvesting. [$^3$H]-thymidine uptake was determined with a Wallac 1450 MicroBeta Liquid Scintillation Counter. As shown in FIG. 3, treatment with (11R)-71-85, but not (11R)-Ctrl, led to a dose-dependent decrease in T cell proliferation in response to T cell receptor (TCR) stimulation.

To evaluate cytokine production, T cells were purified from spleen and stimulated with anti-CD3 plus anti-CD28 for 3 days. Cells were then left unstimulated overnight and treated with 1 or 2 μM (11R)-71-85 or control peptide (11R)-Ctrl, or with DMSO only. After treatment, cells were restimulated with either anti-CD3 plus anti-CD28 (to stimulate the TCR and the alternative p38 pathway), or PMA plus ionomycin supplemented with monensin (to stimulate the classical p38 pathway). Cytokine expression was measured by flow-cytometry. As shown in FIGS. 4A-4B, treatment with (11R)-71-85 inhibits the production of TNF-α in response to TCR stimulation, but has no significant effect on cytokine production in response to stimulation with PMA plus ionomycin. The effect of (11R)-71-85 is dose-dependent as treatment with 2 μM (11R)-71-85 inhibits production of TNF-α and IFN-γ to a greater extent than treatment with 1 μM (11R)-71-85.

Inhibition of Th1 and Th17 Differentiation

Additional studies were carried out to evaluate the effect of (11R)-71-85 on T helper (Th) cell differentiation. Expression of IFN-γ and T-bet was used as an indicator of Th1 cells typical of a pro-inflammatory response. Naïve CD4$^+$ T cells were treated with either medium or 2 μM of (11R)-71-85 or (11R)-Ctrl for two hours and after washing, cells were stimulated with anti-CD3 plus anti-CD28 in Th0 (neutral) or Th1 polarizing conditions for 3 days. Cells were treated again with the same concentration of either (11R)-71-85 or (11R)-Ctrl for 2 hours and restimulated with PMA plus ionomycin in the presence of Golgi inhibitor for 4 hours. Expression of T bet and IFNγ was analyzed by flow cytometry (FIGS. 5A-5D). Cells treated with (11R)-71-85 exhibited reduced expression of IFN-γ and T-bet, relative to cells treated with medium or (11R)-Ctrl. These results indicate that treatment with (11R)-71-85 inhibits Th1 differentiation.

The effect of full-length Gadd45α on Th17 differentiation was also evaluated. Purified CD4$^+$ T cells from WT mice were treated with 4 μM of either TAT-Ctrl, TAT-G45FL or TAT-G45Δ10 and stimulated with plate coated anti-CD3 plus anti-CD28 for 48 hours and blotted for the transcription factors NFATc1, IRF4 or IRF8 (FIG. 6A). Treatment of CD4$^+$ T cells with full-length Gadd45α inhibited expression of NFATc1 and IRF4, but not IRF8. Similarly, naïve CD4$^+$ T (CD4$^+$ CD62L$^{hi}$) cells were purified from WT mice and treated with either TAT-Ctrl or TAT-G45FL and stimulated in neutral (Th0) or Th17 skewing conditions (10 ng/ml IL-6+5 ng/ml TGF-β) for 48 hours. The mRNA expression levels of Rorc and Il17a were evaluated (FIG. 6B). Expression of full-length Gadd45α significantly inhibited expression of both Rorc and Il17a under Th17 skewing conditions. These results indicate that full-length Gadd45α inhibits Th17 differentiation.

Example 2

11R-71-85 Inhibits Expression of T Cell Activation Markers In Vivo

The studies described in Example 1 demonstrate that a Gadd45α polypeptide comprising residues 71-85 is capable of inhibiting the alternative p38 activation pathway in vitro and ex vivo. This example describes the finding that a Gadd45α polypeptide comprising residues 71-85 can also inhibit the alternative p38 activation pathway in vivo.

The ability of (11R)-71-85 to inhibit the p38 alternative pathway in vivo was evaluated by assessing expression of interferon regulatory factor 4 (Irf4) mRNA, a transcription factor that is up-regulated following TCR stimulation. (11R)-

71-85 (40 μg) or vehicle control was injected intraperitoneally into wild type mice. Four hours after injection, splenocytes were collected and stimulated with soluble anti-CD3 plus anti-CD28 for 24 hours. Irf4 mRNA expression was assessed by quantitative real time PCR. As shown in FIG. 7, treatment with (11R)-71-85 significantly inhibited expression of Irf4 compared to the control.

Expression of NFATc1 and IRF4, two transcription factors activated upon TCR stimulation, was also evaluated after intravenous (i.v.) injection of (11R)-71-85. WT C57BL/6 mice were injected i.v. with 50 μg of DMSO, (11R)-Scrambled, or (11R)-71-85, and either total T cells or CD4±T cells were purified from spleen at different times. Purified cells were stimulated in vitro with anti-CD3/CD28 for 24 hours and the mRNA levels of Nfatc1 and Irf4 were determined by quantitative real-time PCR. As shown in FIG. 8, treatment with (11R)-71-85 inhibits expression of both Nfat1c and Irf4 following TCR stimulation in total T cells and in CD4±T cells.

Example 3

Administration of 11R-71-85 Inhibits Growth and Vascularization of Pancreatic Tumors, and Inhibits TNF-α Secretion from Tumor-Infiltrating T Cells The p38 MAPK has been implicated in the growth of some tumors that cause local inflammatory responses, such as pancreatic cancer. Therefore, (11R)-71-85 was tested in a pancreatic tumor model. WT C57BL/6 mice were injected with $7.5 \times 10^5$ PANC02 cells. After 16 days, mice received intra-tumor injections of 40 μg or 80 μg (11R)-71-85 or DMSO every other day. Tumor volume from the start of injection (day 16) to day 42 in control mice and mice injected with (11R)-71-85 or DMSO was determined (FIG. 9A). Weight (FIG. 9B) and appearance (FIG. 9C) of the control and treated tumors were assessed on day 38. Both tumor volume and tumor weight were significantly decreased in mice treated with (11R)-71-85 relative to control animals. These results demonstrate that injection of (11R)-71-85 stops the growth of established PANC02 tumors.

The effect of intra-tumor injection of (11R)-71-85 on cytokine secretion from tumor-infiltrating T cells was also evaluated in mice with pancreatic tumors. WT C57BL/6 mice were injected with $7.5 \times 10^5$ PANC02 cells and 16 days later mice received intra-tumor injections of 80 μg of (11R)-71-85 or (11R)-Scrambled every other day for 1 week. Twenty-four hours following the last injection, tumor infiltrating cells were harvested and restimulated with PMA and ionomycin, or left unstimulated, in the presence of Golgi inhibitor for 4 hours. Expression of TNF-α, IFNγ, IL-10 and IL-17 was determined by flow cytometry. As shown in FIG. 10A, TNF-α secretion was reduced after (11R)-71-85 injection in unstimulated cells, which represent their status in vivo. There was no difference in TNF-α secretion after restimulation, which bypasses TCR signaling and activates the classical MAPK cascade. There was no difference between unstimulated and restimulated cells for the other cytokines tested (IFNγ, IL-10, and IL-17; FIGS. 10A-10B).

Tumor vascularization was also assessed in WT mice treated with (11R)-71-85. WT C57BL/6 mice were injected with $7.5 \times 10^5$ PANC02 cells. After 16 days, mice received intra-tumor injections of 80 μg of (11R)-71-85 or (11R)-Scrambled every other day for 2.5 weeks. Twenty-four hours after the last injection, tumors were collected, fixed in formalin, and stained for the endothelial marker CD31, an indicator for tumor vascularization. As shown in FIG. 11, mice treated with (11R)-71-85 exhibited a significant reduction in CD31 staining compared with control treated mice, indicating that administration of (11R)-71-85 inhibits tumor vascularization.

A second murine model of pancreatic cancer was used to evaluate the effect of (11R)-71-85 on cytokine secretion by tumor cells. KPC mice are genetically engineered to develop pancreatic cancer because of oncogene expression and p53 haploinsufficiency. KPC mice were administered 80 μg of either (11R)-71-85 or (11R)-Scrambled by intraperitoneal injection every other day for 1 month. Twenty-four hours after the last injection, tumor infiltrating cells were harvested and restimulated with PMA and ionomycin, or left unstimulated, in the presence of Golgi inhibitor for 4 hours. Expression of intracellular TNF-α was determined by flow cytometry (FIG. 12). The results demonstrate that administration of (11R)-71-85 inhibits TNF-α secretion by tumor-infiltrating T cells.

Example 4

(11R)-71-85 Inhibits Progression of PanIN and Cancer Formation in KPC Mice

KPC mice provide a genetic model of murine pancreatic tumors that closely mimics the human disease. KPC (KrasG12D/+; LSLTrp53R172H/+; Pdx-1-Cre) mice express K-ras in pancreatic epithelium, and when made heterozygous for p53, develop spontaneous tumors starting at approximately 8-10 weeks of age (Hingorani et al., *Cancer Cell* 7(5):469-483, 2005). This involves the formation of pancreatic intraepithelial neoplasia precursor lesions (PanIN) and progression to fully-developed carcinoma with surrounding stromal and inflammatory reactions (Hingorani et al., *Cancer Cell* 7(5):469-483, 2005). Histologic examination of pancreatic tissue from 8-13 week old KPC mice revealed PanIN in various stages of development, defined by histological changes of the pancreatic ductal epithelium as well as the formation of a surrounding fibroinflammatory reaction, as well as areas of fully developed invasive carcinoma. As seen in human disease, infiltrating T cells were found in these lesions. Notably, in T-cell-rich regions one could easily detect mononuclear cells that stained with antibodies specific for p38 pY323, the defining phosphorylation site for the alternative pathway, and TNFα, which were absent in T cell-poor regions.

Figure 13A:
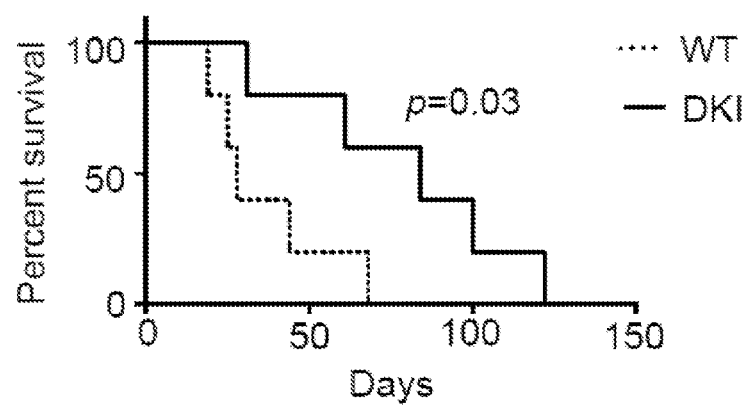

To ask if T cells in which TCR-signaled p38 activation is involved in tumorigenesis, 6 week old KPC mice were sub-lethally irradiated and reconstituted with WT or DKI bone marrow. The former developed invasive cancer and died with a mean time of survival of 37±9 days (FIG. 13A). In contrast, mice that received DKI bone marrow survived much longer, with a mean of 80±16 days (FIG. 13A). Therefore, genetic ablation of the p38 alternative pathway reduced the progression of oncogene-mediated pancreatic cancer.

Figure 13B:
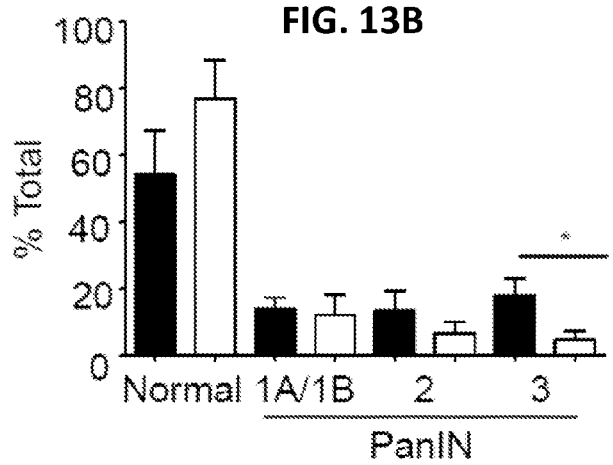
Figure 13C:
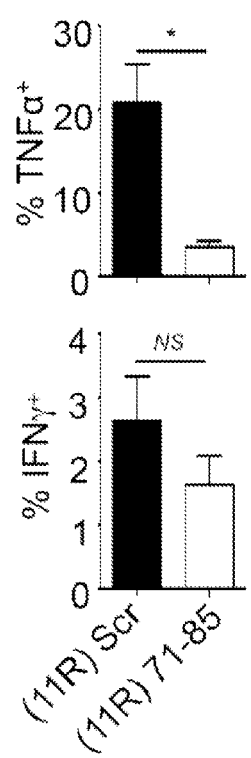
Figure 13D:
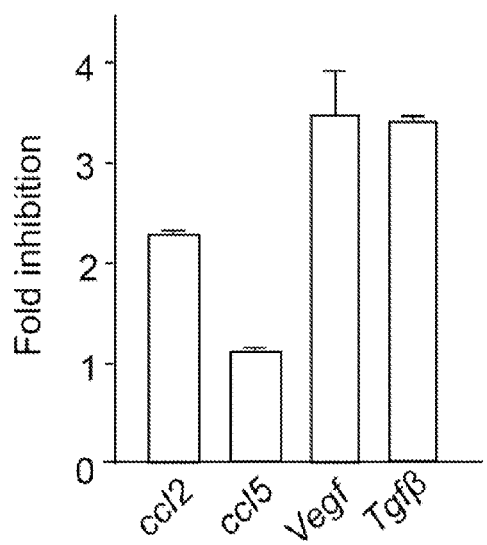

Given these findings, further experiments were conducted to determine if inhibition of the alternative pathway in KPC mice would alter disease progression. KPC mice were treated with intravenous (11R)-71-85 or (11R)-Scrambled starting at 9 weeks of age, and the pancreas was histologically evaluated 3.5 weeks later. Thirty-three percent (2 of 6) of mice treated with (11R)-Scrambled developed invasive carcinoma in the pancreas. In contrast, no mice treated with (11R)-71-85 showed signs of invasiveness. Histologic evaluation of H&E stained sections showed a reduced intrapancreatic fibro-inflammatory reaction in (11R)-71-85 treated compared to (11R)-Scrambled treated tumors. (11R)-71-85 not only prevented the formation of invasive carcinoma, but it also slowed the progression towards high grade PanIN formation (PanIN3, carcinoma in situ) (FIG. 13B). Similar to the PANC02 model, tumor infiltrating lymphocytes (TIL) from KPC mice treated with (11R)-71-85 had reduced numbers of $CD4^+$ cells expressing TNFα compared to control, whereas the expression of IFNγ was slightly reduced (FIG. 13C). In line with the reduced TNFα secretion, Irf4 mRNA expression was decreased in $CD4^+$ TILs after (11R)-71-85 treatment. Consistent with this, expression of Ccl2, Ccl5, Vegf, and Tgfβ was also reduced in pancreatic epithelial cells of KPC mice (FIG. 13D). The fact that early stage PanIN formation was present, but later pre-invasive stages were reduced, in (11R)-71-85-treated mice supports a role for T cell-derived TNFα in the progression of PanIN towards invasive carcinoma.

Example 5

High Levels of pY323 p38 in Human PDAC TIL Indicates a Poor Prognosis

The importance of p38 alternative activation in murine pancreatic cancer, and in particular the oncogene-driven KPC mice, prompted studies to address whether this pathway might be involved in human pancreatic ductal adenocarcinoma (PDAC) as well. Pancreatic tissue from 193 patients with histologically-verified PDAC was analyzed for infiltrating p38 pY323-positive cells. In all samples there was marked infiltration of T cells that stained with antibodies to p38 pY323, but the number of such cells varied from patient to patient. In the majority of cases (n=153, ~80%), less than 10% of the $CD3^+$ tumor-infiltrating T cells were also positive for pY323, the remainder having ≥10% of their T cells expressing p38 pY323. The p38 pY323-positive T cells also expressed TNFα, as detected in sequential tumor sections. Double immunofluorescence supported these findings, demonstrating that p38 pY323-positive T cells produced TNFα. Patients having infiltrates with more than 10% p38 pY323-positive T cells had a statistically-significant shorter survival (median survival of 296 days post-diagnosis) compared to patients with less than 10% p38 pY323-positive cells (median survival of 613 days post-diagnosis) (FIG. 14A). There was no such correlation with other clinical or pathological findings (age, gender, tumor size, TNM stage, histological grading, UICC stage, number of tumor positive lymph nodes). There was also no difference in the amount of T cell infiltration between the two groups, indicating that activation of the p38 alternative pathway, not simply the presence of infiltrating T cells, correlates with outcome (FIG. 14B). The density of CD31-positive tumor vessels was examined in 10 randomly selected patients with high and 10 randomly selected patients with low numbers of p38 pY323-positive T cells. The former had a statistically significant increase in vascularization (FIG. 14C), indicating that p38 alternative activation in TIL leads to tumor neovascularization, a known predictor of poor survival in PDAC.

Example 6

Evaluation of Gadd45α Polypeptides in an Animal Model of Multiple Sclerosis (MS)

This example describes an animal model of multiple sclerosis to evaluate the effect of treatment with a Gadd45α polypeptide. The experimental autoimmune encephalomyelitis (EAE) mouse model is a recognized model of CNS-relevant demyelinating autoimmune disease. Methods of inducing EAE, and animal models that naturally develop EAE, are well known in the art (see, for example, Matsushita et al., J. Clin. Invest. 118(10):3420-3430, 2008; Grewal et al., Immunity 14:291-302, 2001; Tran et al., Eur. J. Immunol. 30:1410-1415, 2000; or Butzkueven et al., Nat. Med. 8:613-619, 2002; and U.S. Patent Application Publication No. 2008/0166318). The C57BL/6 EAE model is generally representative of chronic and progressive MS.

EAE is induced in C57BL/6 female mice by immunization with approximately 200 μg of myelin oligodendrocyte protein (MOG) 35-55 peptide in complete Freund's adjuvant containing 4 mg/mL of Mycobacterium tuberculosis per mouse by subcutaneous injection. Pertussis toxin is administered intraperitoneally at day 0 and day 2 after immunization. At varying stages after immunization, mice are administered a Gadd45α polypeptide or vehicle alone.

Mice are examined for signs of EAE daily. EAE is scored using a 5 point scale (0, no paralysis; 1, limp tail; 2, hind limb paresis and difficulty righting itself; 3, hind limb paralysis; 4, hind limb and forelimb paralysis; and 5, moribund). A decrease in the average score following treatment with the Gadd45α polypeptide, relative to vehicle alone, indicates that the Gadd45α polypeptide is effective for promoting myelination and treating MS. Imaging techniques can also be used to assess the degree of myelination at varying stages.

Example 7

Evaluation of Gadd45α Polypeptides in MS Patients

This example describes a method to evaluate the use of Gadd45α polypeptides in humans. The method involves the use of ocular coherence tomography (OCT) and magnetic resonance imaging (MRI) to study myelination of the retinal nerve fiber layer (RNFL).

Optic neuritis, a common manifestation of MS, often occurs as the initial manifestation of central nervous system demyelination, or develops during the course of disease. Since the RNFL is composed only of unmyelinated axons, measuring RNFL thickness represents a viable method of monitoring axonal loss in MS patients. OCT is a noninvasive, noncontact, accurate, and reproducible technique that quantitates the thickness of the peripapillary RNFL, fovea, and macula. RNFL is evaluated in MS patients prior to and following treatment with a Gadd45α polypeptide. An increase in axonal thickness following treatment with the Gadd45α polypeptide indicates that the Gadd45α polypeptide is effective for promoting myelination and treatment of MS.

Example 8

Assessment of the Efficacy of Gadd45α Polypeptides for the Treatment of MS

This example describes methods for the assessment of the efficacy of Gadd45α polypeptides for the treatment of MS.

Subjects having MS are treated with a composition comprising a Gadd45α polypeptide. One of skill in the art is capable of determining an appropriate dose and dosing schedule of Gadd45α polypeptide compositions. Subjects are assessed for measures of MS described below prior to initiation of therapy, periodically during the period of therapy and at the end of the course of treatment.

The efficacy of the Gadd45α polypeptide compositions in subjects with multiple sclerosis can be assessed by the following measures:

1. MRI measures, such as:
   $T_2$ lesion load
   Volume of $T_1$ hypointensities
   N-acetyl aspartate (NAA) levels
   Whole brain atrophy 2. Clinical measures, specifically:
Change in EDSS (Expanded Disability Status Scale)
Change in SRS (Scripps Neurological Rating Scale)
Relapse rate
9-hole peg test
3. Immunologic measures, specifically:
Markers of Th1 and Th2 T cell lineages
FACS analysis of various T cell markers
Cytokine production by T cells in vitro
Proliferation of T cells
$T_2$ Lesion Load The analyses on $T_2$ lesion load include the following:
comparison of the mean volume of $T_2$ lesions during the pre-treatment period to the mean volume of $T_2$ lesions during the treatment period
comparison of the mean volume of $T_2$ lesions during the pre-treatment period to the mean volume of $T_2$ lesions during the last 4 weeks of the treatment period Volume of $T_1$ Hypointensities The analyses on volume of $T_1$ hypointensities include the following:
comparison of the mean volume of $T_1$ hypointensities during the pre-treatment period to the mean volume of $T_1$ hypointensities during the treatment period
comparison of the mean volume of $T_1$ hypointensities during the pre-treatment period to the mean volume of $T_1$ hypointensities during the last 4 weeks of the treatment period

EDSS

Baseline EDSS score is determined for subjects prior to start of treatment. EDSS is measured periodically during the course of treatment. The change from baseline EDSS to EDSS during the treatment period is determined. Also, change from baseline scores for SRS and the 9-hole peg test during the treatment period are determined.

Relapses

The frequency of relapses over the 2 years prior to receiving treatment with the Gadd45α polypeptide are compared to the frequency of relapses while being treated with the Gadd45α polypeptide.

The effectiveness of therapy comprising administration of Gadd45α polypeptide compositions in subjects with MS is demonstrated by a reduction in the average number of MS exacerbations per subject in a given period (such as 6, 12, 18 or 24 months) compared with a period prior to treatment. A reduction in the average rate of increase in the subject's disability score over some period (e.g., 6, 12, 18 or 24 months) as measured, for example, by the EDSS score, or even an improvement in the disability score, also demonstrates the effectiveness of the Gadd45α polypeptide therapy.

Example 9

Evaluation of Gadd45α Polypeptides in an Animal Model of Rheumatoid Arthritis

This example describes an animal model of rheumatoid arthritis to evaluate the effect of treatment with a Gadd45α polypeptide. The collagen-induced arthritis (CIA) model is the most commonly used animal model to study rheumatoid arthritis. Methods of inducing autoimmune arthritis in this model are well known in the art (see, for example, Jirmanova et al., *Blood* 118(12):3280-3289, 2011; Brand et al., *Nat Protoc* 2(5):1269-1275, 2007).

In this example, arthritis is induced by injecting 10 week-old H-2$^r$ mice with 100 μg bovine type II collagen emulsified in complete Freund's adjuvant (CFA) at the base of the tail, and boosting 21 days later with 100 μg bovine type II collagen emulsified in incomplete Freund's adjuvant (IFA). After induction of arthritis, mice are administered a Gadd45α polypeptide or vehicle alone. Each paw is scored as follows: 0, no evidence of erythema; 1, erythema and mild swelling confined to tarsals; 2, erythema and mild swelling extending from the ankle to midfoot; 3, swelling extending from the ankle to metatarsal joints; 4, severe swelling/ankylosis of the whole foot. A decrease in the average score following treatment with the Gadd45α polypeptide, relative to vehicle alone, indicates that the Gadd45α polypeptide is effective for the treatment of rheumatoid arthritis.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated growth arrest and DNA-damage-inducible alpha (Gadd45α) polypeptide no more than 25 amino acids in length, wherein the amino acid sequence of the polypeptide comprises LQIHFTLIXAFCCEN (SEQ ID NO: 1), wherein X is Q or R.

2. The isolated Gadd45α polypeptide of claim 1 which is no more than 20 amino acids in length.

3. The isolated Gadd45α polypeptide of claim 1, comprising the amino acid sequence LQIHFTLIQAFCCEN (SEQ ID NO: 2) or LQIHFTLIRAFCCEN (SEQ ID NO: 3).

4. The isolated Gadd45α polypeptide of claim 1, consisting of the amino acid sequence LQIHFTLIQAFCCEN (SEQ ID NO: 2) or LQIHFTLIRAFCCEN (SEQ ID NO: 3).

5. A fusion protein comprising the Gadd45α polypeptide of claim 1 and a heterologous peptide.

6. The fusion protein of claim 5, wherein the heterologous peptide is a cell-penetrating peptide (CPP).

7. The fusion protein of claim 6, wherein the CPP comprises poly-arginine.

8. The fusion protein of claim 7, wherein poly-arginine comprises or consists of 11 arginine (11R) residues.

9. The fusion protein of claim 8, consisting of 11R fused to the N-terminus of the Gadd45α polypeptide.

10. The fusion protein of claim 8, consisting of 11R fused to the amino acid sequence LQIHFTLIQAFCCEN (SEQ ID NO: 2) or LQIHFTLIRAFCCEN (SEQ ID NO: 3).

11. A composition comprising the polypeptide of claim 1 and a pharmaceutically acceptable carrier.

12. An in vitro or ex vivo method of inhibiting proliferation of T cells in response to T cell receptor stimulation, or of inhibiting differentiation of T cells into Th1 or Th17 cells, comprising contacting the T cells with the polypeptide of claim 1, thereby inhibiting proliferation of the T cells, or inhibiting differentiation of the T cells.

13. The method of claim 12 which is an ex vivo method, wherein the T cells have been isolated from a subject and the isolated T cells are contacted with the polypeptide or fusion protein.

14. A method for inhibiting proliferation of T cells in response to T cell receptor stimulation in a subject, or for inhibiting differentiation of T cells into Th1 or Th17 cells in a subject, comprising administering to the subject the polypeptide of claim 1.

15. A method for treating a subject with a T cell- and/or p38-mediated autoimmune or inflammatory disorder, comprising selecting a subject with a T cell- and/or p38-mediated autoimmune or inflammatory disorder and administering to the subject a therapeutically effective amount of the polypeptide of claim 1, thereby treating the subject.

16. The method of claim 15, wherein the T cell- and/or p38-mediated autoimmune or inflammatory disorder comprises multiple sclerosis, rheumatoid arthritis or pancreatic cancer.

17. The method of claim 15, wherein the polypeptide is administered by intravenous, intra-tumor or intraperitoneal administration.

18. The method of claim 15, wherein the T cell- and/or p38-mediated autoimmune or inflammatory disorder comprises pancreatic cancer and the polypeptide is administered by intra-tumor injection.

19. A method for inhibiting tumor vascularization in a subject, comprising selecting a subject with a tumor and administering to the subject a therapeutically effective amount of the polypeptide of claim 1, thereby inhibiting tumor vascularization in the subject.

20. The method of claim 19, wherein the tumor is a pancreatic tumor.

21. The method of claim 19, wherein the polypeptide is administered by intra-tumor administration.

* * * * *